(12) United States Patent     (10) Patent No.: US 8,158,774 B2
Kitagawa et al.     (45) Date of Patent: Apr. 17, 2012

(54) METHOD FOR INTRODUCING A NUCLEIC-ACID PROTECTING GROUP

(75) Inventors: Hidetoshi Kitagawa, Tsukuba (JP); Kouichi Uetake, Tsukuba (JP)

(73) Assignee: Nippon Shinyaku Co., Ltd., Kyoto (JP)

( * ) Notice: Subject to any disclaimer, the term of this patent is extended or adjusted under 35 U.S.C. 154(b) by 498 days.

(21) Appl. No.: 12/375,755

(22) PCT Filed: Aug. 1, 2007

(86) PCT No.: PCT/JP2007/065070
§ 371 (c)(1),
(2), (4) Date: Jan. 30, 2009

(87) PCT Pub. No.: WO2008/016079
PCT Pub. Date: Feb. 7, 2008

(65) Prior Publication Data
US 2009/0286970 A1     Nov. 19, 2009

(30) Foreign Application Priority Data
Aug. 2, 2006    (JP) ................................. 2006-210439

(51) Int. Cl.
*C07H 21/00*     (2006.01)
(52) U.S. Cl. ..................... 536/25.3; 536/25.31
(58) Field of Classification Search ........................ None
See application file for complete search history.

(56) References Cited

U.S. PATENT DOCUMENTS
6,586,615 B1    7/2003   Kettner et al.
2007/0282097 A1   12/2007   Ohgi et al.

FOREIGN PATENT DOCUMENTS
WO    WO-02054931    7/2002
WO    WO-02088062   11/2002
WO    WO-2005023828   3/2005
WO    WO-2006022323   3/2006

OTHER PUBLICATIONS

Matysiak et al. Helvetica Chimica Acta (1998), vol. 81, pp. 1545-1566.*
Tadaaki Ohgi at al., A new RNA synthetic method with a 2'-O-(2-cyanoethoxymethyl) Protecting Group), Org. Lett. 2005, 7(16), 3477-3480.
Maruzen et al., "The Chemical Society of Japan", 4th Edition, Jikken Kagaku Koza 19, p. 476; reference dated Jun. 5, (Japanese Era year) Heisei 4 (please see last page of reference); which is Jun. 5, 1992 in the Western calendar. "Concise explanation of relevance" in English, of p. 476, prefaces the reference as submitted.

* cited by examiner

*Primary Examiner* — Patrick Lewis
(74) *Attorney, Agent, or Firm* — McDermott Will & Emery LLP

(57) ABSTRACT

The present invention relates to a simple, economical method for introducing substituent (I) at the 2'-hydroxyl group of the ribose of a ribonucleic acid derivative whose 3'-hydroxyl group and 5'-hydroxyl group are protected with a silicon protecting group, wherein $WG^1$ represents an electron-withdrawing group:

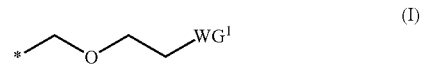

The invention also relates to a method for producing a ribonucleic acid derivative of formula (3), comprising the reaction of a ribonucleic acid derivative of formula (1) with a monothioacetal compound of formula (2) to produce the ribonucleic acid derivative of formula (3), using iodine as the reagent for halogenating the sulfur atom of the monothioacetal compound of formula (2) in the presence of an acid:

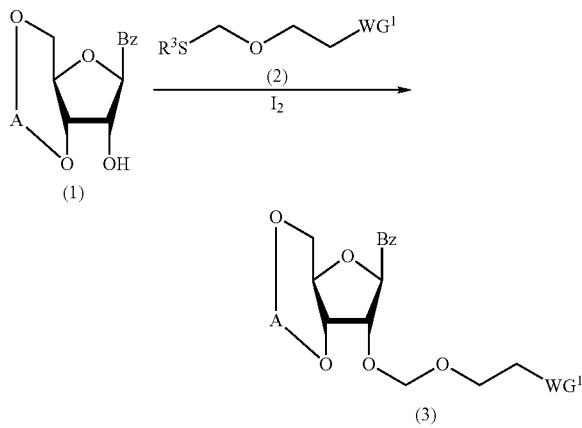

In formulae (1), (2), and (3), Bz represents a nucleobase which may or may not have a protecting group; $WG^1$ represents an electron-withdrawing group; $R^3$ represents alkyl or aryl; and A represents a silicon substituent.

15 Claims, No Drawings

METHOD FOR INTRODUCING A NUCLEIC-ACID PROTECTING GROUP

This application is a U.S. national phase application under 35 U.S.C. §371 of International Patent Application No. PCT/JP2007/065070, filed Aug. 1, 2007, and claims the benefit of Japanese Patent Application No. 2006-210439, filed Aug. 2, 2006. The International Application was published in Japanese on Feb. 7, 2008 as WO 2008/016079. The disclosures of all the prior applications are hereby incorporated by reference in their entireties.

FIELD OF THE INVENTION

The present invention relates to a method for introducing the following substituent (I) at the 2'-hydroxyl group of the ribose in a ribonucleic acid derivative whose 3'-hydroxyl group and 5'-hydroxyl group are protected with a silicon protecting group.

[Chemical scheme 1]

(I)

In formula (I), $WG^1$ represents an electron-withdrawing group.

The "electron-withdrawing group" of $WG^1$ includes, for example, cyano, nitro, alkylsulfonyl, arylsulfonyl, and halogen. Among these, cyano is preferable.

The "alkyl" moiety in "alkylsulfonyl" of $WG^1$ includes, for example, a straight or branched alkyl with one to 5 carbon atoms. Specifically, the alkyl moiety includes, for example, methyl, ethyl, n-propyl, isopropyl, n-butyl, isobutyl, sec-butyl, tert-butyl, n-pentyl, isopentyl, neopentyl, and tert-pentyl.

The "aryl" moiety in "arylsulfonyl" of $WG^1$ includes, for example, an aryl with 6 to 12 carbon atoms. Specifically, the aryl moiety includes, for example, phenyl, 1-naphthyl, 2-naphthyl and biphenyl. The aryl may optionally have a substituent. The substituent includes, for example, halogen, alkyl, alkoxy, cyano and nitro. The aryl may be substituted with one to three such substituents at any appropriate positions.

The "halogen" of $WG^1$ includes, for example, fluorine, chlorine, bromine and iodine.

The "halogen" and the "alkyl" as substituents of "aryl" of $WG^1$ are the same as those described for the "halogen". The "alkoxy" as the substituent of "aryl" of $WG^1$ includes, for example, a straight or branched alkoxy with one to 4 carbon atoms. Specifically, the alkoxy includes, for example, methoxy, ethoxy, n-propoxy, isopropoxy, n-butoxy, isobutoxy, sec-butoxy, and tert-butoxy. Among these, the alkoxy with one to 3 carbon atoms is preferable.

BACKGROUND

Oligo RNA is useful as RNA probes for gene analysis, pharmaceutical RNA materials (antisense RNA, ribozymes, RNA for control of gene expression through RNAi), artificial enzymes, and aptamers. As reagents for use in the preparation of the oligo RNA, phosphoramidite compounds substituted at the 2'-hydroxyl group of the ribose with the 2-cyanoethoxymethyl (CEM) group, which can be removed under neutral conditions, have been reported (Ohgi et al., Organic Letters, Vol. 7, 3477 (2005); WO 2006/022323 A1).

The production of the phosphoramidite compounds includes a step for introducing CEM as a protecting group at the 2'-hydroxyl group of the ribose. This step has so far been performed by reacting a ribonucleic acid derivative (raw material) protected with a silicon protecting group (for example, tetraisopropyldisiloxan-1,3-diyl) at the 3'- and 5'-hydroxyl groups of the ribose, with methylthiomethyl 2-cyanoethyl ether as an alkylating reagent and N-iodosuccinimide (NIS) or N-bromosuccinimide (NBS) as a reagent (oxidant) for halogenating the sulfur atom in the alkylating reagent, in the presence of an acid such as trifluoromethanesulfonic acid or silver trifluoromethanesulfonate (WO 2006/022323 A1).

Since the reagent described above for halogenating the sulfur atom in the alkylating reagent and the acids described above, namely NIS, NBS, trifluoromethanesulfonic acid and silver trifluoromethanesulfonate, are highly reactive compounds, the nucleobase in the ribonucleic acid derivative as the raw material compound may also possibly be halogenated, even when the reaction temperature is lowered to about 0° C. Therefore, it is necessary to carry out the reaction at very low temperatures of −50° C. to −40° C., so as to prevent the halogenation of the nucleobase. On a small scale (for example, when the amount of the ribonucleic acid derivative as the raw material compound is about 100 mg to about 2 g), the reaction may sometimes proceed smoothly even when the reaction temperature is around 0° C.

When NIS and NBS are used, byproducts derived from the succinimide are generated. It is very hard to remove these byproducts by extraction procedures. Generally, it is necessary to remove the byproducts by column chromatography, which is unsuitable for large-scale purification.

Furthermore, NIS, NBS, trifluoromethanesulfonic acid, and silver trifluoromethanesulfonate are very expensive reagents and so carry an economic disadvantage.

Therefore, such conventional processes using NIS and NBS as those described above are not suitable for large-scale production of the phosphoramidite compounds.

DETAILED DESCRIPTION OF THE INVENTION

Problems to be Solved by the Invention

It is an object of the invention to provide an economical and simple method for introducing the following substituent (I) (for example, the CEM group) at the 2'-hydroxyl group of the ribose in a ribonucleic acid derivative whose 3'-hydroxyl group and 5'-hydroxyl group are protected with a silicon protecting group.

[Chemical scheme 2]

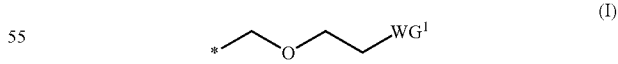

(I)

In formula (I), $WG^1$ has the same meaning as described above.

The inventors have intensively studied to accomplish the object mentioned above, and the inventors found that the problems could be overcome. Thus, the invention has been achieved.

The present invention includes, for instance, a method for producing a ribonucleic acid derivative represented by the following general formula (3), comprising the reaction of a ribonucleic acid derivative represented by the following general formula (1) with a monothioacetal compound represented by the following general formula (2) to produce the ribonucleic acid derivative represented by the following general formula (3), wherein iodine is used as the reagent for halogenating the sulfur atom of the monothioacetal compound (2) in the presence of an acid.

[Cheimical scheme 3]

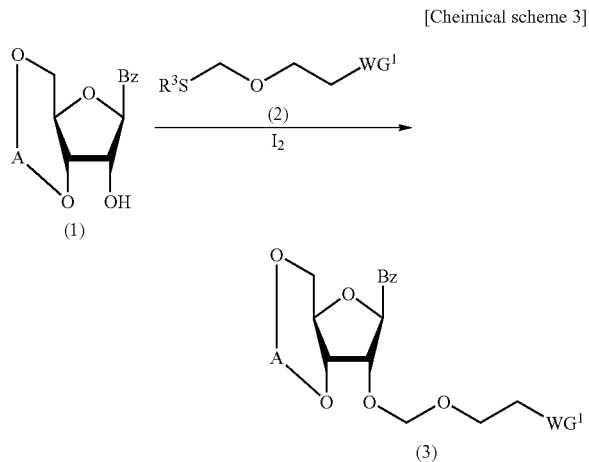

In formulae (1), (2), and (3), Bz represents a nucleobase which may have a protecting group; $WG^1$ has the same meaning as described above; $R^3$ represents alkyl or aryl; and A represents a silicon substituent represented by the following general formula (4a) and (4b).

[Chemical scheme 4]

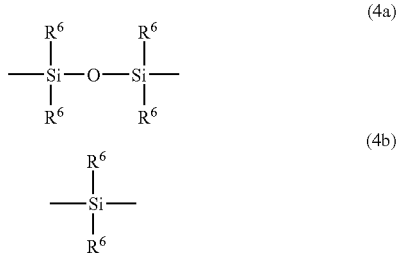

In formulae (4a) and (4b), $R^6$ represents alkyl.

The "nucleobase" Bz is not particularly limited as long as it is a nucleobase to be used in the synthesis of a nucleic acid. The nucleobase may include, for example, pyrimidine bases such as cytosine and uracil; purine bases such as adenine and guanine; or modified forms thereof.

The "nucleobase" Bz may optionally be protected. Especially, in the nucleobases with the amino group, for example, adenine, guanine and cytosine, the amino group is preferably protected. The "protecting group for the amino group" is not particularly limited as long as it is a protecting group to be used as a protecting group of a nucleic acid, and it may include, for example, benzoyl, 4-methoxybenzoyl, acetyl, propionyl, butyryl, isobutyryl, phenylacetyl, phenoxyacetyl, 4-tert-butylphenoxyacetyl, 4-isopropylphenoxyacetyl, and (dimethylamino)methylene.

The "modified form" of Bz means a nucleobase substituted with appropriate substituents, which include, for example, halogen, acyl, alkyl, arylalkyl, alkoxy, alkoxyalkyl, hydroxy, amino, monoalkylamino, dialkylamino, carboxy, cyano and nitro. The modified form means a nucleobase substituted with one to three such substituents at any appropriate positions.

The "halogen" for the "modified form" of Bz may include, for example, fluorine, chlorine, bromine and iodine.

The "acyl" for the "modified form" of Bz may include, for example, a straight or branched alkanoyl with one to 6 carbon atoms and an aroyl with 7 to 13 carbon atoms. Specifically, the acyl may include formyl, acetyl, n-propionyl, isopropionyl, n-butyryl, isobutyryl, tert-butyryl, valeryl, hexanoyl, benzoyl, naphthoyl, and levulinyl.

The "alkyl" for the "modified form" of Bz may include, for example, a straight or branched alkyl with one to 5 carbon atoms. Specifically, the alkyl may include, for example, methyl, ethyl, n-propyl, isopropyl, n-butyl, isobutyl, sec-butyl, tert-butyl, n-pentyl, isopentyl, neopentyl, and tert-pentyl. The alkyl may optionally have a substituent, which includes, for example, halogen, alkyl, alkoxy, cyano and nitro. The alkyl may be substituted with one to three such substituents at appropriate positions.

The "alkyl" moiety in the "arylalkyl", "alkoxyalkyl", "monoalkylamino", "dialkylamino" and "alkylsulfonyl" for the "modified form" of Bz is the same as those for the "alkyl" as described above.

The "alkoxy" for the "modified form" of Bz may include, for example, a straight or branched alkoxy with one to 4 carbon atoms. Specifically, the alkoxy may include, for example, methoxy, ethoxy, n-propoxy, isopropoxy, n-butoxy, isobutoxy, sec-butoxy, and tert-butoxy. Especially, the alkoxy with one to 3 carbon atoms is preferable. Methoxy is particularly preferable.

The "alkoxy" moiety in the "alkoxyalkyl" for the "modified form" of Bz is the same as those for the "alkoxy" as described above.

The "aryl" moiety in the "arylalkyl" for the modified form of Bz may include, for example, an aryl group with 6 to 12 carbon atoms. Specifically, the aryl may include, for example, phenyl, 1-naphthyl, 2-naphthyl, and biphenyl. The aryl may have a substituent, which includes, for example, halogen, alkyl, alkoxy, cyano and nitro. The aryl may be substituted with one to three such substituents at any appropriate positions.

The "halogen", the "alkyl", and the "alkoxy" as the substituents for the "alkyl" and the "aryl" for the "modified form" of Bz are the same as described above.

The "alkyl" and the "aryl" of $R^3$ are respectively the same as those for the "alkyl" and the "aryl" for the modified form of Bz.

A specific example of the monothioacetal compound (11) is 2-cyanoethyl methylthiomethyl ether.

The "alkyl" of $R^6$ may include, for example, a straight or branched alkyl with one to 5 carbon atoms. Specifically, the alkyl may include, for example, methyl, ethyl, n-propyl, isopropyl, n-butyl, isobutyl, sec-butyl, tert-butyl, n-pentyl, isopentyl, neopentyl, and tert-pentyl.

In an additional aspect of the invention, the method for producing a ribonucleic acid derivative represented by the following general formula (3) comprising the reaction of a ribonucleic acid derivative represented by the following general formula (1) with a monothioacetal compound represented by the following general formula (2) may include a method for producing a phosphoramidite compound (hereinafter referred to as phosphoramidite compound (A)) represented by the following general formula (A) comprising a step for producing a ribonucleic acid derivative represented by the following general formula (3), using iodine as a reagent for halogenating the sulfur atom in the monothioacetal compound (2) in the presence of an acid.

[Chemical scheme 5]

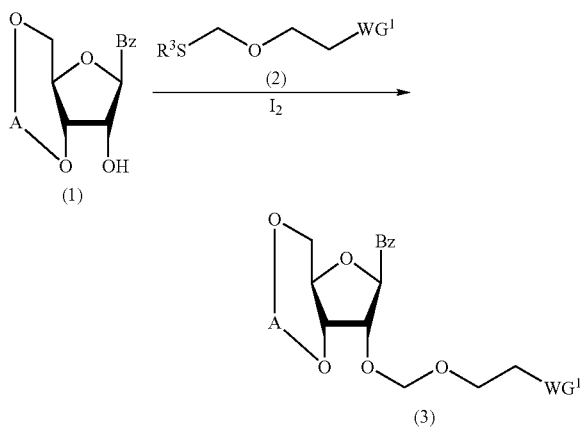

In formulae (1), (2), and (3), A, Bz, $R^3$ and $WG^1$ have the same meanings as described above.

[Chemical scheme 6]

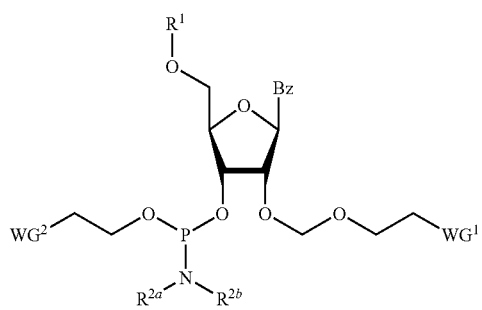

In formula (A), Bz and $WG^1$ have the same meanings as described above. $R^{2a}$ and $R^{2b}$ may be the same or different and each represents alkyl, or $R^{2a}$ and $R^{2b}$ may form a 5- or 6-membered saturated cyclic amino group when combined together with the adjacent nitrogen atom. The saturated cyclic amino group may have one oxygen atom or one sulfur atom as a ring member in addition to the nitrogen atom. $WG^2$ may be the same or different and represents an electron-withdrawing group; and $R^1$ represents a substituent represented by the following general formula (5).

[Chemical scheme 7]

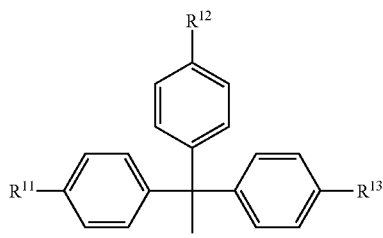

In formula (5), $R^{11}$, $R^{12}$ and $R^{13}$ may be the same or different and each represents hydrogen or alkoxy.

The "alkoxy" of $R^{11}$, $R^{12}$ and $R^{13}$ is the same as those described above for the "alkoxy" for the modified form of Bz.

The "alkyl" of $R^{2a}$ and $R^{2b}$ is the same as those described above for the "alkyl" for the modified form of Bz.

The "saturated 5- or 6-membered cyclic amino group" of $R^{2a}$ and $R^{2b}$ may include, for example, pyrrolidin-1-yl, piperidin-1-yl, morpholin-4-yl and thiomorpholin-4-yl.

The "electron-withdrawing group" of $WG^2$ is the same as those described above for the "electron-withdrawing group" of $WG^1$.

The phosphoramidite compound (A) is a phosphoramidite compound protected with the following substituent (I) at the 2'-hydroxyl group of the ribose. Because the group introduced at the 2'-hydroxyl group is a straight substituent and because the configuration around the phosphorus atom bound to the 3'-hydroxyl group is not crowded, the condensation reaction in the synthesis of oligo RNA can proceed very quickly compared with the phosphoramidite compounds conventionally used, so that the phosphoramidite compound (A) has the characteristic feature of a good condensation yield. The use of the phosphoramidite compound (A) can lead to the production of oligo RNA of high purity through almost the same procedures as those used for producing oligo DNA.

[Chemical scheme 8]

In formula (I), $WG^1$ has the same meaning as described above.

Herein, the "oligo RNA" in accordance with the invention means an oligo nucleic acid containing at least one ribonucleic acid (RNA) as a monomer constituting the oligo nucleic acid. In addition, the "oligo DNA" means an oligo nucleic acid that contains no ribonucleic acid (RNA) as a monomer constituting the oligo nucleic acid.

The Invention is Now Described in More Detail.

If a raw material has a substituent (for example, hydroxy, amino, carboxy) that would affect the reaction by the method described below, the raw material is protected in advance with an appropriate protecting group by a known method before the reaction is carried out. The protecting group can be removed by a known method such as catalytic reduction, alkali treatment or acid treatment.

I. Method for Preparing Ribonucleic Acid Derivative (3)

The method can be carried out by reacting a ribonucleic acid derivative represented by the following general formula (1) with a monothioacetal compound represented by the following general formula (2) in the presence of an acid and iodine.

[Chemical scheme 9]

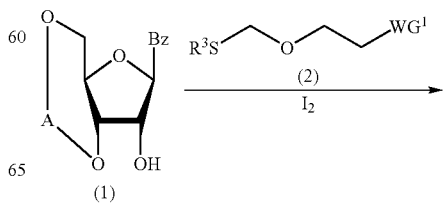

-continued

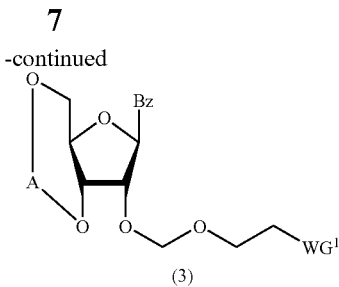

(3)

In formulae (1), (2), and (3), A, Bz, $R^3$ and $WG^1$ have the same meanings as described above.

The monothioacetal compound (2) can be produced by known methods (for example, the International Publication WO 2006/022323 A1 pamphlet).

The method can be carried out by reacting a ribonucleic acid derivative (1) commercially available or synthesizable according to any method described in references with the monothioacetal compound (2) and iodine in the presence of an acid. The amount of "iodine" to be used in the method is suitably in the range of 0.8 to 20 mol per mol of the ribonucleic acid derivative (1), and preferably in the range of one to 10 mol per mol thereof. The reaction temperature is suitably in the range of −20° C. to 20° C., preferably in the range of −10° C. to 10° C., and more preferably in the range of −5° C. to 5° C. The reaction time depends on the kind of raw material and the reaction temperature. Generally, however, the reaction time is suitably in the range of 5 min to 5 h. The amount of the "monothioacetal compound (2)" to be used in the method is suitably in the range of 0.8 to 5 mol per mol of the ribonucleic acid derivative (1), preferably in the range of 1 to 3 mol per mol thereof. As the acid, any organic acid that can activate the alkylating reaction at the 2'-position of the ribose and that is acidic enough to form a salt with a base moiety of the nucleic acid, with no specific limitation, is satisfactory. Satisfactory examples of such acids are methanesulfonic acid, trifluoromethanesulfonic acid, or mixtures thereof. In particular, methanesulfonic acid or a mixture of trifluoromethanesulfonic acid and methanesulfonic acid is preferable. The amount of the acid to be used is suitably in the range of 0.01 to 10 mol per mol of the ribonucleic acid derivative (I), and preferably in the range of 0.1 to 5 mol per mol thereof. When a mixture of trifluoromethanesulfonic acid and methanesulfonic acid is used, trifluoromethanesulfonic acid is suitably in the range of 0.01 to 0.9 mol per mol of methanesulfonic acid, preferably in the range of 0.02 to 0.5 mol per mol thereof, and more preferably in the range of 0.05 to 0.2 mol per mol thereof. The solvent to be used is not specifically limited unless it is involved in the reaction, and may include, for example, dichloromethane, chloroform, carbon tetrachloride, 1,2-dichloroethane, benzene, toluene, xylene, tetrahydrofuran (hereinafter referred to as "THF"), acetonitrile, N,N-dimethylformamide, or appropriate mixtures thereof. In particular, THF is preferable.

II. Method for Producing Phosphoramidite Compound (A)

By carrying out the following steps "a" to "d", the phosphoramidite compound (A) can be produced from known compounds or from readily producible intermediates.

The Method is Now Described in Detail.

(1) Step a:

This step is the same as the method described above in I.

(2) Step b:

This step is a step for producing a ribonucleic acid derivative represented by the following formula (7), by dissolving the ribonucleic acid derivative (3) produced in step "a" in an appropriate solvent and then treating the resulting solution with a reagent for removing the silicon substituent.

[Chemical scheme 10]

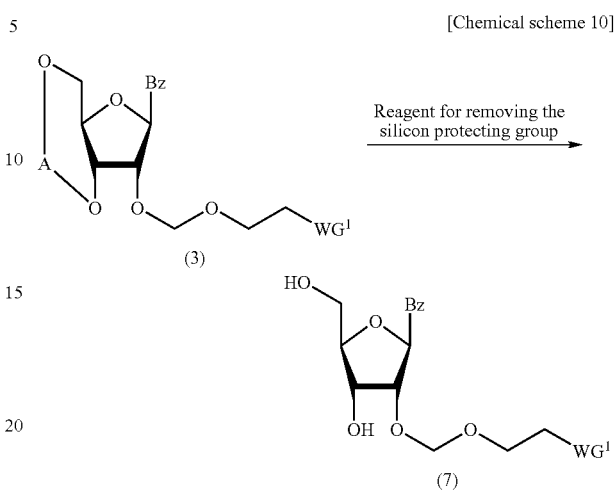

In formulae (3) and (7), A, Bz and $WG^1$ have the same meanings as described above.

The "reagent for removing the silicon substituent" to be used in the step may include tetrabutylammonium fluoride, a salt of an amine with hydrogen fluoride, or a mixture of an amine and hydrogen fluoride at an appropriate ratio in an appropriate solvent.

Sometimes, in addition, the step is carried out by using a mixed reagent prepared by adding an additional appropriate acid to a salt of an amine with hydrogen fluoride or a mixture of an amine and hydrogen fluoride at an appropriate ratio in an appropriate solvent. The acid to be used in such cases includes, for example, acetic acid, hydrochloric acid and sulfuric acid. The amount of such acid to be used is suitably in the range of 0.01 to 10 mol per mol of an amine, preferably in the range of 0.1 to 5 mol per mol thereof.

The solvent to be used includes, for example, THF, acetonitrile, methanol, isopropanol, toluene, dimethylsulfoxide, N,N-dimethylformamide or appropriate mixtures thereof. THF and methanol are particularly preferable.

The amount of the "reagent for removing the silicon substituent" that can be used in this step depends on the kind of ribonucleic acid derivative (3), the reagent to be used for removing the silicon substituent, and the solvent to be used. The reagent is used suitably in the range of 1 to 10 mol per mol of the ribonucleic acid derivative (3), and preferably in the range of 1.2 to 1.5 mol per mol thereof. The reaction temperature is suitably in the range of 0° C. to 80° C. The reaction time depends on the kind of ribonucleic acid derivative (3), the reagent for to be used removing the silicon substituent, the solvent to be used, and the reaction temperature. Generally, the reaction time is suitably in the range of 30 min to 10 h.

After completion of the reaction, the reaction mixture is left to stand or an appropriate volume of water is added to it and it is then left to cool. In this manner, the ribonucleic acid derivative (7) can be obtained as a precipitate. The volume of water to be added is suitably in the range of 0.05 to 5 times the volume of the solvent used, preferably in the range of 0.06 to 1 times the volume thereof, and more preferably in the range of 0.07 to 0.1 times the volume thereof.

The "salt of an amine with hydrogen fluoride" to be used in this step may include, for example, ammonium fluoride, trimethylamine hydrofluoride, trimethylamine dihydrofluoride, trimethylamine trihydrofluoride, trimethylamine tetrahydrofluoride, trimethylamine pentahydrofluoride, trimethylamine hexahydrofluoride, triethylamine hydrofluoride, triethylamine dihydrofluoride, triethylamine trihydrofluoride, triethylamine tetrahydrofluoride, triethylamine 26 hydrofluoride, quinuclidine trihydrofluoride, and triethylenediamine tetrahydrofluoride (see, for example, Journal Molecular Structure, 193, 247 (1989), Pol. J. Chem, 67 (2), 281 (1993), Chem. Europ. J., 4 (6), 1043 (1998), J. Fluorine Chem., 118 (1-2), 123, (2002)). In particular, ammonium fluoride and triethylamine trihydrofluoride are preferable.

Furthermore, the "mixture of an amine and hydrogen fluoride at an appropriate ratio in an appropriate solvent" includes, for example, mixtures of amines, such as ammonia, triethylamine, triethylamine, quinuclidine, and triethylenediamine, and hydrogen fluoride in an appropriate solvent (for example, THF, acetonitrile, methanol, isopropanol, and toluene) at a molar ratio of amine:hydrogen fluoride in the range of, for example, 1:1 to 1:30.

(3) Step c:

The step is a step for allowing $R^1X^3$ (8) to react with a ribonucleic acid derivative (7) according to a known method, and producing a ribonucleic acid derivative (9) by introducing a protecting group ($R^1$), which can be removed under acidic conditions, at the 5'-hydroxyl group of the ribonucleic acid derivative (7) produced in Step b.

[Chemical scheme 11]

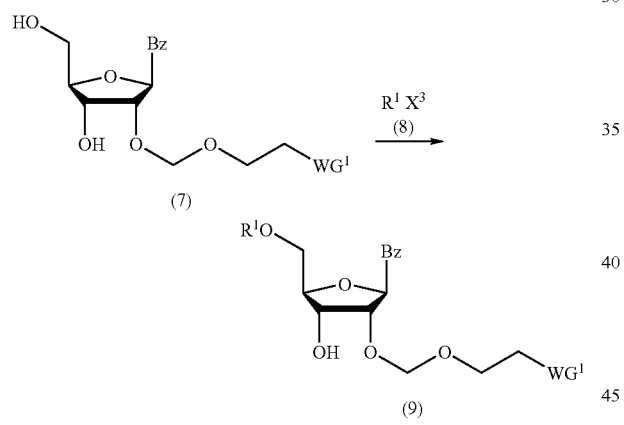

In formulae (7), (8), and (9), $B_Z$, $R^1$ and $WG^1$ have the same meanings as described above. $X^3$ represents halogen.

The "halogen" of $X^3$ is the same as those described above for the "halogen" for modified form of $B_Z$.

The amount of $R^1X^3$ (8) to be used may be in the range of 0.8 to 20 mol per mol of the ribonucleic acid derivative (7), and preferably in the range of 1 to 10 mol per mol thereof. The solvent to be used is not specifically limited unless it is involved in the reaction, and may include, for example, acetonitrile and THF. The "base" may include organic bases such as pyridine, 2,6-dimethylpyridine, 2,4,6-trimethylpyridine, N-methylimidazole, triethylamine, tributylamine, N,N-diisopropylethylamine and 1,8-diazabicyclo[5.4.0]-7-undecene.

The amount of the base to be used may be in the range of 0.8 to 20 mol per mol of the ribonucleic acid derivative (7), and preferably in the range of 1 to 10 mol per mol thereof. The reaction temperature is preferably in the range of 0° C. to 120° C. The reaction time depends on the kind of raw materials and the reaction temperature, and is preferably between 30 min and 24 h.

(4) Step d:

The step is a step for producing the phosphoramidite compound (A), whose 3'-hydroxyl group is phosphoramidited, by allowing a phosphoramiditing reagent and an activating agent, if necessary, to act on the ribonucleic acid derivative (9) produced in Step c.

[Chemical scheme 12]

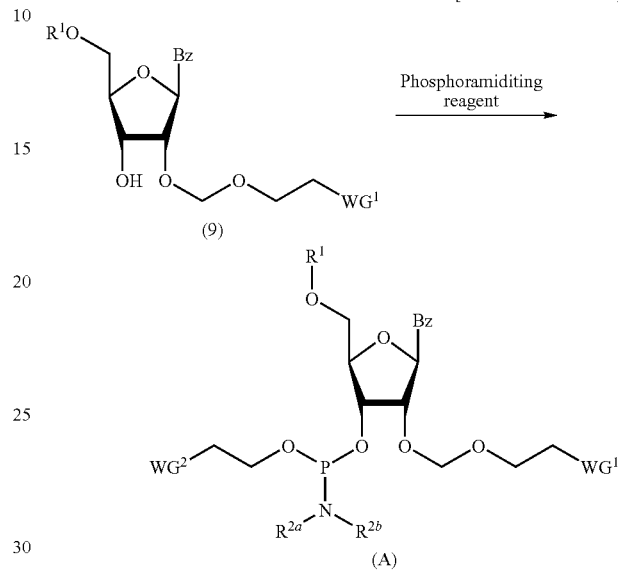

In formulae (9) and (A), $B_Z$, $R^1$, $R^{2a}$, $R^{2b}$, $WG^1$ and $WG^2$ have the same meanings as described above.

The "phosphoramiditing reagent" may include a compound represented by the following general formulae (10a) and (10b).

[Chemical scheme 13]

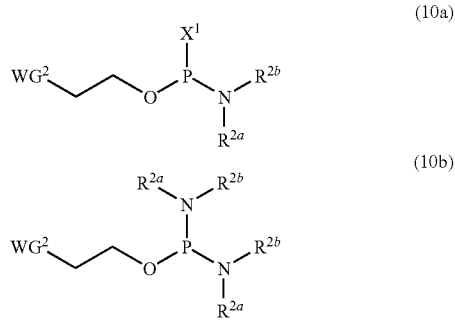

In formulae (10a) and (10b), $R^{2a}$, $R^{2b}$ and $WG^2$ have the same meanings as described above. $X^1$ represents halogen.

The "halogen" of $X^1$ may include the same as those described above for the "halogen" for the modified form of $B_Z$.

The solvent to be used is not specifically limited unless it is involved in the reaction, and may include, for example, acetonitrile and THF. The amount of the phosphoramiditing reagent to be used may be in the range of 0.8 to 20 mol per mol of the ribonucleic acid derivative (9), and preferably in the range of 1 to 10 mol per mol thereof. The "activating agent" may include 1H-tetrazole, 5-ethylthiotetrazole, 5-benzylmercapto-1H-tetrazole, 4,5-dichloroimidazole, 4,5-dicyanoimidazole, benzotriazole triflate, imidazole triflate, pyridinium triflate, N,N-diisopropylethylamine and 2,4,6-collidine/N-methylimidazole. The amount of the activating agent to be used may be in the range of 0.8 to 20 mol per mol of the ribonucleic acid derivative (9), and preferably in the range of 1 to 10 mol per mol thereof. The reaction temperature is preferably in the range of 0° C. to 120° C. The reaction time depends on the kind of raw material and the reaction temperature, and is preferably between 30 min and 24 h.

The phosphoramidite compound (A) thus produced can be isolated and purified by a general method such as concentration, liquid phase conversion, partition, solvent extraction, crystallization, recrystallization, fractional distillation or chromatography.

II. A Method for Producing Oligo RNA

Oligo RNA represented by the following general formula (B) (hereinafter referred to as "oligo RNA (B)") can be produced by using the phosphoramidite compound (A).

The details are described below.

[Chemical scheme 14]

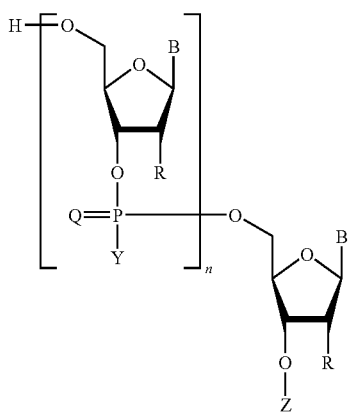

(B)

In formula (B), each B represents independently a nucleobase or a modified form thereof. Each Q independently represents O or S. Each R independently represents H, hydroxyl, halogen, alkoxy, alkylthio, alkylamino, dialkylamino, alkenyloxy, alkenylthio, alkenylamino, dialkenylamino, alkynyloxy, alkynylthio, alkynylamino, dialkynylamino or alkoxyalkyloxy, and at least one R is hydroxyl. Each Y represents alkyl, alkoxy, alkylthio, O$^-$, S$^-$, NR$^{2a}$R$^{2b}$ (R$^{2a}$ and R$^{2b}$ have the same meanings as described above). When R in the nucleic acid monomer unit constituting the oligo RNA (B) is hydroxyl, Y represents O$^-$. Z represents H, a phosphate group or a thiophosphate group. n represents an integer in the range of 1 to 200.

n is preferably an integer in the range of 10 to 100, and more preferably an integer in the range of 15 to 50.

The "nucleobase" of B is not particularly limited as long as it is a nucleobase to be used in the synthesis of a nucleic acid, and examples thereof may include pyrimidine bases such as cytosine, uracil and thymine, purine bases such as adenine and guanine. The "modified form" of B is a group in which a nucleobase has been substituted by an arbitrary substituent.

The "substituent" for the modified form of B may include halogen, acyl, alkyl, arylalkyl, alkoxy, alkoxyalkyl, hydroxyl, amino, monoalkylamino, dialkylamino, carboxy, cyano and nitro. The modified form of B may be substituted by 1 to 3 of these substituents at arbitrary positions.

The "halogen", "acyl", "alkyl", "arylalkyl", "alkoxy", "alkoxyalkyl" "amino", "monoalkylamino" and "dialkylamino" for the modified form of B are the same as those described above for the modified form of B$_Z$, respectively.

The "alkyl" moiety in the "alkyl", "alkoxy", and "alkylthio" of Y is the same as those described above for the modified form of B$_Z$, respectively.

The "halogen", "alkoxy", "alkylamino" and "dialkylamino" of R are the same as those described above for the modified form of B$_Z$, respectively.

The "alkyl" moiety in the "alkoxyalkyloxy" and "alkylthio" of R is the same as those described above for the "alkyl" for the modified form of B$_Z$.

The "alkoxy" moiety in the "alkoxyalkyloxy" of R is the same as those described above for the "alkoxy" for the modified form of B$_Z$.

The "alkenyl" in the "alkenyloxy", "alkenylthio", "alkenylamino" and "dialkenylamino" of R may include straight or branched alkenyl having 2 to 6 carbon atoms. Specifically, the alkenyl may include, for example, vinyl, allyl, 1-propenyl, isopropenyl, 1-butenyl, 2-butenyl, 1-pentenyl and 1-hexenyl.

The "alkynyl" moiety in the "alkynyloxy", "alkynylthio", "alkynylamino" and "dialkynylamino" of R may include straight or branched alkynyl having 2 to 4 carbon atoms. Specifically, the alkynyl may include, for example, ethynyl, 2-propynyl and 1-butynyl.

Herein, "a nucleic acid monomer unit" represents each part of nucleic acid constituting oligo RNA (B) and each (oligo) nucleic acid derivative.

A method for producing oligo-RNA (B) using phosphoramidite compound (A) can be performed by a known method, for example, by condensing a nucleic acid monomer compound to step by step in the 3' to 5' direction according to the following Steps A to G. In the method for producing the oligo-RNA mentioned above, it is possible to produce an oligo-RNA (B) wherein one or more R groups are hydroxyl groups. For example, in process B mentioned below, it is possible to produce an oligo-RNA (B) in which all of the R groups are hydroxyl groups, by using solely the phosphoramidite compound (A) as a nucleic acid monomer compound.

Compounds and reagents to be used in the following steps except the phosphoramidite compound (A) are not particularly limited as long as they are generally used in syntheses of oligo-RNAs or oligo-DNAs. In addition, all the steps can be performed by using an automatic DNA synthesizer or manually as in the case of using conventional reagents for synthesizing a nucleic acid. The use of an automatic synthesizer is desirable from the point of view of the simplicity and ease of the method and the accuracy of the synthesis.

(1) Step A:

The step is a step for producing an (oligo)nucleic acid derivative represented by the following general formula (12) by removing the 5'-hydroxyl group from an (oligo)nucleic acid derivative represented by the following general formula (11) by allowing an acid for removing to R$^1$ to act on the (oligo)nucleic acid derivative (11).

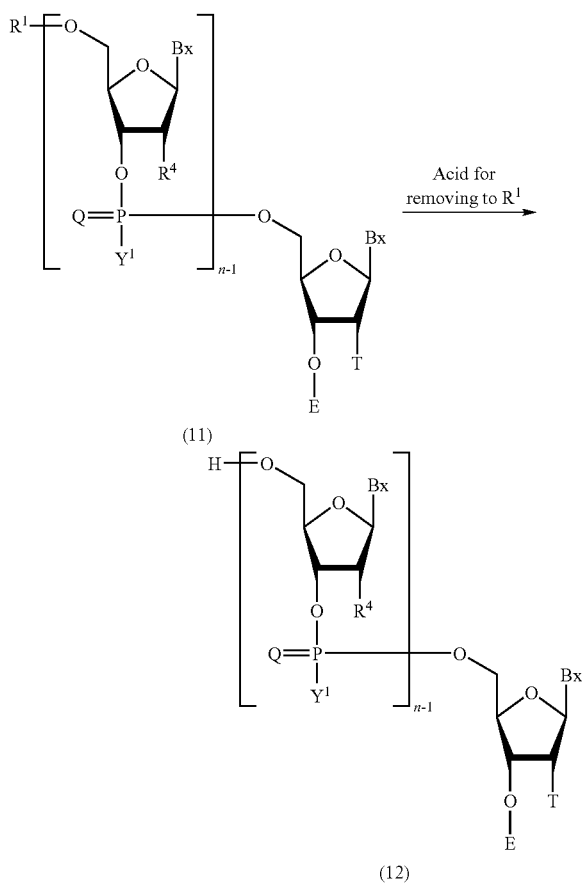

(11)

(12)

In formulae (11) and (12), n, each Q and $R^1$ has the same meanings as described above. Each $B_X$ independently represents a nucleobase which may have protecting groups, or a modified form thereof. Each $R^4$ independently represents H, halogen, alkoxy, alkylthio, alkylamino, dialkylamino, alkenyloxy, alkenylthio, alkenylamino, dialkenylamino, alkynyloxy, alkynylthio, alkynylamino, dialkynylamino, alkoxyalkyloxy or the substituent represented by the following general formula (13).

[Chemical scheme 16]

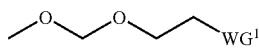

(13)

In formula (13), $WG^1$ has the same meanings as described above.

Each $Y^1$ represents alkyl, alkoxy, alkylthio, $NR^{2a}R^{2b}$ ($R^{2a}$ and $R^{2b}$ have the same meanings as described above) or the substituent represented by the following general formula (14).

[Chemical scheme 17]

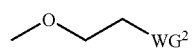

(14)

In formula (14), $WG^2$ have the same meanings as described above.

When $R^4$ in the nucleic acid monomer unit constituting the (oligo) nucleic acid derivatives (11) and (12) is a substituent represented by the above general formula (13), $Y^1$ represents a substituent represented by the above general formula (14).

E represents acyl and a substituent represented by the following general formula (15).

[Chemical scheme 18]

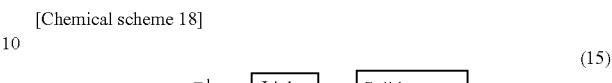

(15)

In formula (15), $E^1$ represents a single bond or a substituent represented by the following general formula (16).

[Chemical scheme 19]

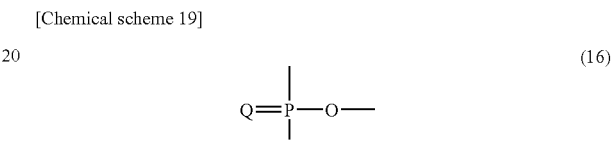

(16)

In formula (16), Q and $Y^1$ have the same meanings as described above.

T represents H, acyloxy, halogen, alkoxy, alkylthio, alkylamino, dialkylamino, alkenyloxy, alkenylthio, alkenylamino, dialkenylamino, alkynyloxy, alkynylthio, alkynylamino, dialkynylamino, alkoxyalkyloxy, an substituent represented by the above general formula (13) or a substituent represented by the above general formula (15), with the proviso that either E or T is a substituent (15).

The "nucleobase" $B_X$ is not particularly limited as long as it is a nucleobase to be used in the synthesis of a nucleic acid, and examples thereof may include pyrimidine bases such as cytosine, uracil, and thymine, purine bases such as adenine and guanine.

The "nucleobase" $B_X$ may be protected, and particularly in the case of a nucleobase having an amino group such as adenine, guanine or cytosine, the amino group thereof is preferably protected.

The "protecting group of amino group" is not particularly limited as long as it is a protecting group to be used as a protecting group of a nucleic acid, and examples thereof may include benzoyl, 4-methoxybenzoyl, acetyl, propionyl, butyryl, isobutyryl, phenylacetyl, phenoxyacetyl, 4-tert-butylphenoxyacetyl, 4-isopropylphenoxyacetyl and (dimethylamino)methylene.

The "modified form" of $B_X$ is a group in which a nucleobase has been substituted by an arbitrary substituent. The "substituent" for the modified form of $B_X$ may include halogen, acyl, alkyl, arylalkyl, alkoxy, alkoxyalkyl, hydroxyl, amino, monoalkylamino, dialkylamino, carboxy, cyano and nitro. The modified form of B may be substituted by 1 to 3 of these substituents at arbitrary positions.

The "halogen", "acyl", "alkyl", "arylalkyl", "alkoxy", "alkoxyalkyl", "monoalkylamino" and "dialkylamino" for the modified form of $B_X$ are the same as those described above for the modified form of $B_Z$.

The "halogen", "alkoxy", "alkylamino" and "dialkylamino" of $R^4$ are the same as those described above for the modified form of $B_Z$.

The "alkyl" moiety in the "alkoxyalkyloxy" and "alkylthio" of $R^4$ is the same as those described above for the "alkyl" for the modified form of $B_Z$.

The "alkoxy" moiety in the "alkoxyalkyloxy" of $R^4$ is the same as those described above for the "alkoxy" for the modified form of $B_Z$.

The "alkenyl" moiety in "alkenyloxy", "alkenylthio", "alkenylamino", and "dialkenylamino" of $R^4$ is the same as those described above for the "alkenyl" of R.

The "alkynyl" moiety in the "alkynyloxy" "alkynylthio", "alkynylamino" and "dialkynylamino" of $R^4$ is the same as those described above for the "alkynyl" of R.

The "amino", "alkylamino", "alkenylamino" or "alkynylamino" of $R^4$ may be protected. The protecting group of the amino group is not particularly limited as long as it is a protecting group to be used as a protecting group of an amino group, and examples thereof may include trifluoroacetyl, benzoyl, 4-methoxybenzoyl, acetyl, propionyl, butyryl, isobutyryl, phenylacetyl, phenoxyacetyl, 4-tert-butylphenoxyacetyl, 4-isopropylphenoxyacetyl and (dimethylamino) methylene. In particularly, trifluoroacetyl is preferred.

The "acyl" of E is the same as those described above for the "acyl" for the modified form of $B_Z$.

The "acyl" moiety in "acyloxy" of T is the same as those described above for the "acyl" for the modified form of $B_Z$.

The "halogen", "alkoxy", "alkylamino" and "dialkylamino" of T are the same as those described above for the modified form of $B_Z$.

The "alkyl" moiety in the "alkoxyalkyloxy" and "alkylthio" related to the T may include the same ones as those illustrated for the "alkyl" related to the above-mentioned modified form of $B_Z$.

The "alkoxy" moiety in the "alkoxyalkyloxy" of T is the same as those described above for the "alkoxy" for the modified form of $B_Z$.

The "alkenyl" moiety in "alkenyloxy", "alkenylthio", "alkenylamino" and "dialkenylamino" of T is the same as those described above for the "alkenyl" of R.

The "alkynyl" moiety in "alkynyloxy" "alkynylthio", "alkynylamino", "alkylamino" and "dialkynylamino" of T is the same as those described above for the "alkynyl" of R.

The "alkyl" moiety in "alkyl", "alkoxy" and "alkylthio" of $Y^1$ is the same as those described above for the "alkyl" of $B_Z$.

The step is performed by allowing an acid to act on a compound represented by the following formula (17a), (17b) (a nucleic acid derivative (11) wherein n is 1) which is attached to the solid support, or an oligo-RNA or an oligo-DNA produced by performing Step A through Step D (oligonucleic acid derivative (18) wherein n is 2 to 100) which is attached to the solid support (hereinafter referred to as the "oligonucleic acid attached the solid support").

In formulae (17a) and (17b), $B_X$ and $R^1$ have the same meanings as described above. $R^{2L}$ and $R^{4L}$ represent substituent (21). $R^2$ represents acyloxy. $R^{4a}$ represents H, acyloxy, halogen, alkoxy, alkylthio, alkylamino, dialkylamino, alkenyloxy, alkenylthio, alkenylamino, dialkenylamino, alkynyloxy, alkynylthio, alkynylamino, dialkynylamino, alkoxyalkyloxy or substituent (13).

The "acyl" moiety in the "acyloxy" of $R^2$ and $R^{4a}$ is the same as those described above for the "acyl" for the modified form of $B_Z$.

The "halogen", "alkoxy", "alkylamino" and "dialkylamino" of $R^{4a}$ are the same as those described above for the modified form of $B_Z$.

The "alkyl" moiety in "alkoxyalkyloxy" and "alkylthio" of $R^{4a}$ is the same as those described above for the "alkyl" for the modified form of $B_Z$.

The "alkoxy" moiety in the "alkoxyalkyloxy" of $R^{4a}$ is the same as those described above for the "alkoxy" for the modified form of $B_Z$.

The "alkenyl" moiety in "alkenyloxy", "alkenylthio", "alkenylamino" and "dialkenylamino" of $R^{4a}$ is the same as those described above for the "alkenyl" of R.

The "alkynyl" moiety in the "alkynyloxy", "alkynylthio", "alkynylamino" and "dialkynylamino" of $R^{4a}$ is the same as those described above for the "alkynyl" of R.

The "amino", "alkylamino", "alkenylamino" and "alkynylamino" of $R^{4a}$ may be protected. The protecting group of the amino group is not particularly limited as long as it is a protecting group to be used as a protecting group of an amino group, and examples thereof may include trifluoroacetyl, benzoyl, 4-methoxybenzoyl, acetyl, propionyl, butyryl, isobutyryl, phenylacetyl, phenoxyacetyl, 4-tert-butylphenoxyacetyl, 4-isopropylphenoxyacetyl and (dimethylamino) methylene. Particularly, trifluoroacetyl is preferred.

Examples of the "solid support" may include a controlled-pore glass (CPG), an oxalyl-controlled pore glass (see, for example, Alul et al., Nucleic Acids Research, Vol. 19, 1527 (1991)), TentaGel support-amino polyethylene glycol derivatization support (see, for example, Wright et al., Tetrahedron Letters, Vol. 34, 3373 (1993)) and a copolymer of porous polystyrene and divinylbenzene.

The "linker" may include 3-aminopropyl, succinyl, 2,2'-diethanol sulfonyl and a long-chain alkylamino (LCAA).

The nucleic acid derivative (17a), nucleic acid derivative (17b) are attached to the solid support, which are produced according to a known method or are commercially available, and examples of a preferable embodiment are a nucleic acid derivative represented by the following general formula (18), (19).

[Chemical scheme 20]

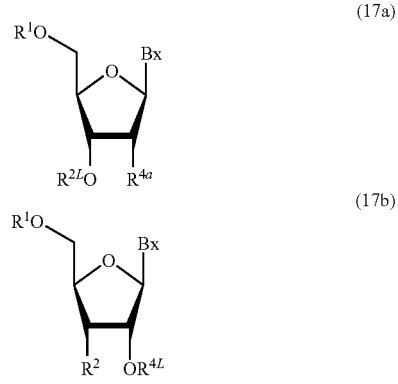

[Chemical scheme 21]

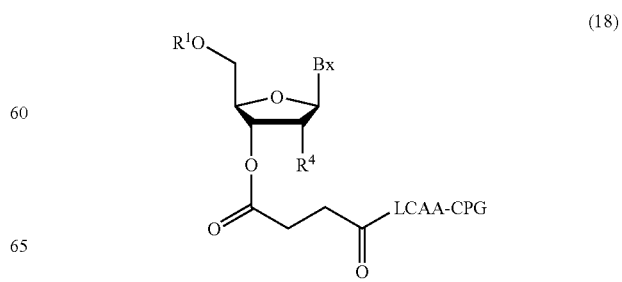

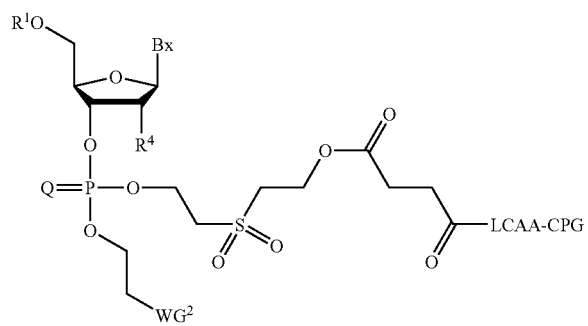

(19)

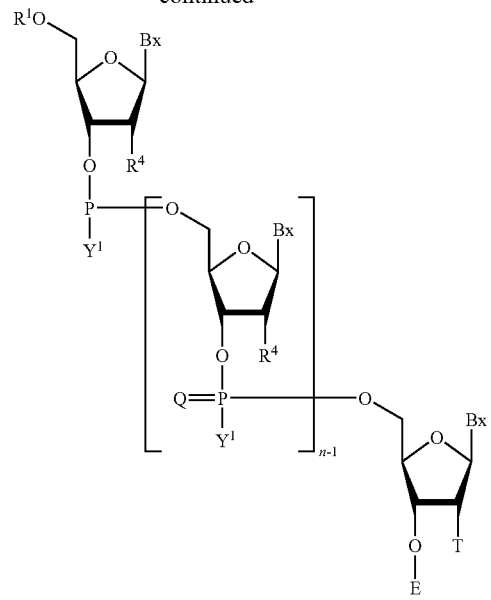

(20)

In formulae (18) and (19), $B_X$, Q, $R^1$, $R^4$ and $WG^2$ have the same meanings as described above.

The nucleic acid derivative (19) wherein $R^4$ is a substituent (13) can be produced from a phosphoramidite compound (A) according to a known method.

The "acid" to be used in the step may include trifluoroacetic acid, dichloroacetic acid and trichloroacetic acid. The acid to be used in the step can be diluted in a suitable solvent so as to be of a concentration of 1% to 5%. The solvent is not specifically limited unless it is involved in the reaction, and may include dichloromethane, acetonitrile, water and an arbitrary mixture thereof. The reaction temperature in the reaction is preferably in the range of 20° C. to 50° C. The reaction time depends on the kind of oligonucleic acid derivative (11), the acid, and the reaction temperature, and is preferably between 1 min and 1 h. The amount of the reagent to be used is preferably in the range of 0.8 to 100 mol per mol of the (oligo)nucleic acid derivative attached to the solid support, and more preferably in the range of 1 to 10 mol per mol thereof.

(2) Step B:

The step is a step for producing an oligonucleic acid derivative represented by the following general formula (20) by condensing a nucleic acid monomer compound with the oligonucleic acid derivative (12) produced in Step A using an activating agent.

In formulae (12) and (20), each $B_X$, E, n, each Q, $R^1$, each $R^4$, T and each $Y^1$ independently have the same meanings as described above. When $R^4$ in the nucleic acid monomer unit constituting the (oligo) nucleic acid derivatives (12) and (20) is a substituent represented by the above general formula (13), $Y^1$ represents a substituent represented by the above general formula (14).

The "nucleic acid monomer compound" may include the phosphoramidite compound (A) and a nucleic acid derivative represented by the following general formula (21).

[Chemical scheme 23]

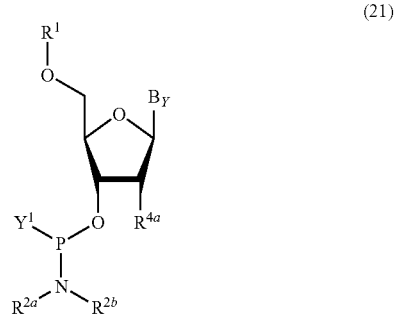

(21)

[Chemical scheme 22]

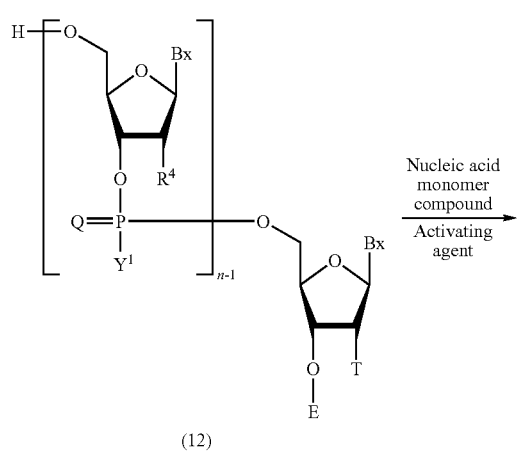

(12)

In formula (21), $R^1$, $R^{2a}$, $R^{2b}$, $R^{4a}$ and $Y^1$ have the same meanings as described above. $B_Y$ represents a nucleobase which may have protecting groups, or a modified form thereof.

The "nucleobase" $B_Y$ is not particularly limited as long as it is a nucleobase to be used in the synthesis of a nucleic acid, and examples thereof may include pyrimidine bases such as cytosine, uracil and thymine, and purine bases such as adenine and guanine.

The "nucleobase" $B_Y$ may be protected, and particularly in the case of a nucleobase having an amino group, such as adenine, guanine or cytosine, the amino group thereof is preferably to be protected.

The protecting group of amino group is not particularly limited as long as it is a protecting group to be used as a protecting group of a nucleic acid, and examples thereof may include benzoyl, 4-methoxybenzoyl, acetyl, propionyl, butyryl, isobutyryl, phenylacetyl, phenoxyacetyl, 4-tert-butylphenoxyacetyl, 4-isopropylphenoxyacetyl and (dimethylamino)methylene.

The "modified form" of $B_Y$ is a group in which a nucleobase has been substituted by an arbitrary substituent. The "substituent" for the modified form of $B_Y$ may include halogen, acyl, alkyl, arylalkyl, alkoxy, alkoxyalkyl, hydroxyl, amino, monoalkylamino, dialkylamino, carboxy, cyano and nitro. The modified form of B may be substituted by 1 to 3 of these substituents at arbitrary positions.

The "halogen", "acyl", "alkyl", "arylalkyl", "alkoxy", "alkoxyalkyl", "monoalkylamino" and "dialkylamino" for the modified form of $B_Y$ are the same as those described above for the modified form of $B_Z$.

The "nucleic acid derivative (21)" may include a nucleic acid compound, which are commercially available or are produced according to a known method (see, for example, Protocols for oligonucleotides and analogs; S. Agrawal, Eds.: Human Press Inc.: Totowa, N.J., 1993).

Examples of the "activating agent" may include the same ones as those illustrated in the above description. The reaction solvent to be used is not specifically limited unless it is involved in the reaction, and may include, for example, acetonitrile and THF.

The reaction temperature is preferably in the range of 20° C. to 50° C. The reaction time depends on the kind of oligonucleic acid derivative (12), the kind of activating agent used, and the reaction temperature, and it is preferably between 1 min and 1 h.

(3) Step C:

The step is a step for allowing a capping agent to react with an oligonucleic acid derivative (12) attached to the solid support in order to cap the 5'-hydroxyl group of the unreacted oligonucleic acid derivative (12) in Step B.

[Chemical scheme 24]

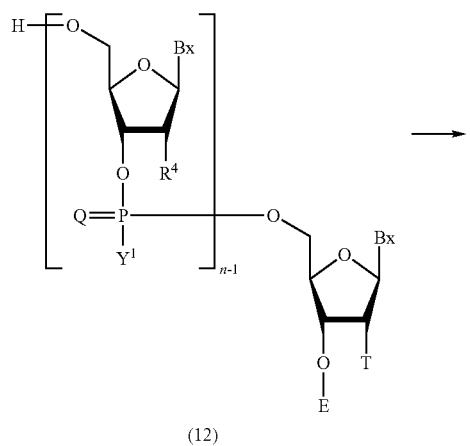

(12)

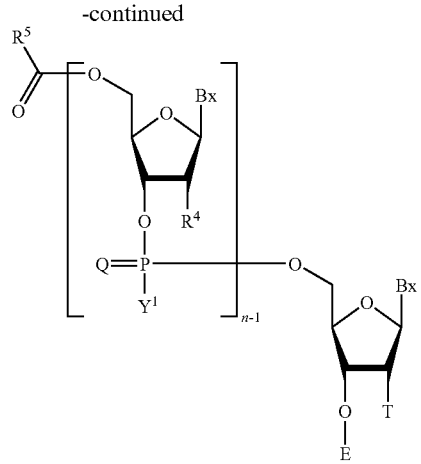

(22)

In formulae (12) and (22), each $B_X$, E, n, each Q, each $R^4$, T, each $Y^1$ have the same meanings as described above. $R^5$ represents methyl, phenoxymethyl and tert-butylphenoxymethyl. When $R^4$ in the nucleic acid monomer unit constituting the (oligo) nucleic acid derivatives (12) and (22) is a substituent represented by the above general formula (13), $Y^1$ represents a substituent represented by the above general formula (14).

The "capping agent" may include acetic anhydride, phenoxyacetic anhydride and tert-butylphenoxyacetic anhydride. The capping agent to be used can be diluted in a suitable solvent so as to be of a concentration of 0.05 to 1 M. The reaction solvent to be used is not specifically limited unless it is involved in the reaction, and may include, for example, pyridine, dichloromethane, acetonitrile, THF and mixtures thereof. In addition, for example, 4-dimethylaminopyridine and N-methylimidazole can be used as a "reaction accelerator" in the step, if necessary. The reaction temperature in the reaction is preferably in the range of 20° C. to 50° C. The reaction time depends on the kind of oligonucleic acid derivative (12), the capping agent, and the reaction temperature, and is preferably between 1 and 30 min. The amount of the capping agent to be used is preferably in the range of 0.8-100 mol per mol of the oligonucleic acid derivative attached to the solid support, and more preferably 1 to 10 mol per mol thereof.

(4) Step D:

The step is a step for converting a phosphite group (trivalent phosphorus) into a phosphate or thiophosphate group (pentavalent phosphorus) by treating the oligonucleic acid derivative (20) produced in Step B with an oxidizing agent.

[Chemical scheme 25]

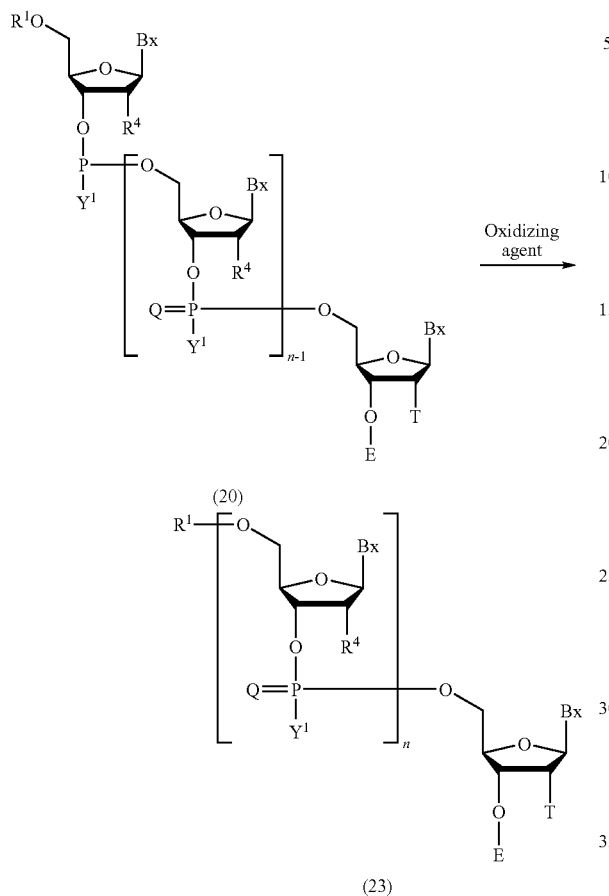

In formulae (20) and (23), each $B_X$, E, n, each Q, $R^1$, each $R^4$, T and each $Y^1$ have the same meanings as described above. When $R^4$ in the nucleic acid monomer unit constituting the (oligo) nucleic acid derivatives (20) and (23) is a substituent represented by the above general formula (13), $Y^1$ represents a substituent represented by the above general formula (14).

When phosphorus is oxidized with oxygen, examples of the "oxidizing agent" may include iodine and tert-butylhydroperoxide. In addition, the oxidizing agent to be used can be diluted in a suitable solvent so as to be of a concentration of 0.05 to 2 M. The reaction solvent to be used is not specifically limited unless it is involved in the reaction, and may include, for example, pyridine, tetrahydrofuran, water and mixtures thereof. For example, iodine/water/pyridine-THF, iodine/pyridine-acetic acid and a peroxidation agent (tert-butylhydroperoxide/dichloromethane and the like) can be used.

In addition, when phosphorus is oxidized with sulfur, examples of the "oxidizing agent" may include sulfur, Beaucage reagent (3H-1,2-benzodithiol-3-on-1,1-dioxide) and 3-amino-1,2,4-dithiazole-5-thione (ADTT). The oxidizing agent to be used can be diluted in a suitable solvent so as to be of a concentration of 0.01 to 2 M. The reaction solvent to be used is not specifically limited unless it is involved in the reaction, and may include, for example, dichloromethane, acetonitrile, pyridine and mixtures thereof.

The amount of the oxidizing agent to be used is preferably in the range of 0.8-100 mol per mol of the oligonucleic acid derivative attached to the solid support, and more preferably in the range of 10 to 50 mol per mol thereof. The reaction temperature is preferably in the range of 20° C. to 50° C. The reaction time depends on the kind of oligonucleic acid derivative (20), the oxidizing agent, and the reaction temperature, and is preferably between 1 and 30 min.

The step is a step for cleaving the oligonucleic acid derivative (23) produced in Step D from the solid support, and then removing the protecting groups of each nucleobase and each phosphate group.

[Chemical scheme 26]

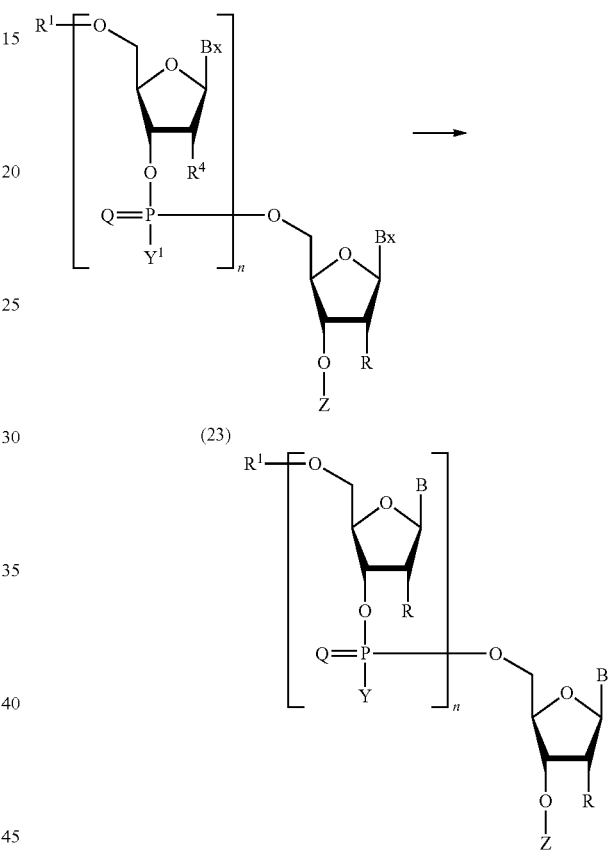

In formulae (23) and (24), each B, each $B_X$, E, each Q, R, $R^1$, each $R^4$, n, T, each Y, each $Y^1$ and Z have the same meanings as described above. When $R^4$ in the nucleic acid monomer unit constituting the (oligo) nucleic acid derivatives (23) and (24) is a substituent represented by the above general formula (13), $Y^1$, Y represent a substituent represented by the above general formula (14) or $O^-$.

The cleavage step is a reaction for cleaving an oligo-RNA having a desired chain length from the solid support and linker with a cleaving agent, and is performed by adding a cleaving agent to the solid support which contains an oligo-RNA having a desired chain length. In the step, the protecting group of a nucleobase can be removed.

The "cleaving agent" may include concentrated aqueous ammonia and methylamine. The cleaving agent to be used in the step may be diluted by, for example, water, methanol, ethanol, isopropyl alcohol, acetonitrile, THF and mixtures thereof. Among these, ethanol is preferable. The concentration of ammonium hydroxide in the solution to be used for deprotection may be 20% to 30% by weight, preferably 25% to 30% by weight, and more preferably 28% to 30% by weight.

The amount of "cleaving agent" to be used in the step may be in the range of 0.8 to 100 mol per mol of the oligonucleic acid derivative attached to the solid support, and preferably in the range of 10 to 50 mol per mol thereof. The reaction temperature may be in the range of 15° C. to 75° C., preferably in the range of 15° C. to 30° C., and more preferably in the range of 18° C. to 25° C. The reaction time for deprotection may be in the range of 10 min to 30 h, preferably 30 min to 24 h, and more preferably 1 to 4 h.

(6) Step F:

The step is a step for producing an oligonucleic acid derivative represented by the following general formula (25) by allowing a reagent for removing the protecting group of the 2'-hydroxyl group of each ribose to act on the oligonucleic acid derivative (24) produced in Step E.

[Chemical scheme 27]

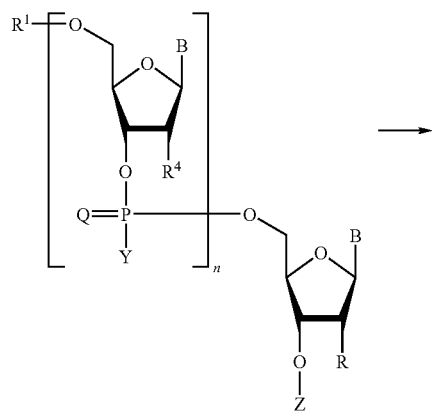

(24)

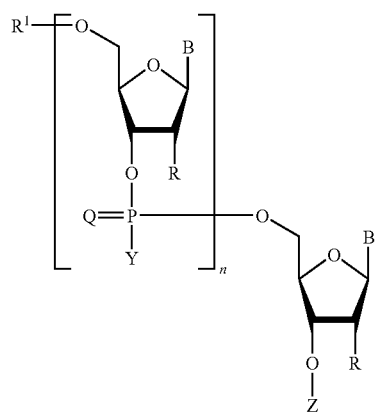

(25)

In formulae (24) and (25), each B, n, each Q, each Y, each R, $R^1$, each $R^4$ and Z have the same meanings as described above. When $R^4$ in the nucleic acid monomer unit constituting the (oligo) nucleic acid derivatives (24) and (25) is a substituent represented by the above general formula (13), Y represents $O^-$.

The "reagent for removing the protecting group of the 2'-hydroxyl group" may include TBAF, and triethylamine/trihydrogenfluoride. The amount of the agent for removing the protecting group of the 2'-hydroxyl group may be in the range of 1 to 500 mol per mol of the protecting group to be removed, and preferably in the range of 5 to 10 mol per mol thereof. The solvent to be used is not specifically limited unless it is involved in the reaction, and may include, for example, THF, N-methylpyrrolidone, pyridine, dimethylsulfoxide and mixtures thereof. The solvent to be used in the reaction may be in the range of 0.8 to 100 mol per mol of the agent for removing the protecting group of the 2'-hydroxyl group, and is preferably in the range of 1 to 10 mol per mol thereof. The reaction temperature is preferably in the range of 20° C. to 80° C. The reaction time depends on the kind of oligonucleic acid derivative (24), the agent for removing the protecting group of the 2'-hydroxyl group to be used, and the reaction temperature, and is preferably in the range of 1 to 100 h.

In addition, nitroalkane, alkylamine, amidine, thiol, thiol derivative and mixture thereof can be added as a scavenger of acrylonitrile, if necessary, to trap the acrylonitrile which is a byproduct in the step. The "nitroalkane" may include straight nitroalkane having 1 to 6 carbon atoms. Specifically, the nitroalkane may include, for example, nitromethane. The "alkylamine" may include straight alkylamine having 1 to 6 carbon atoms. Specifically, the "alkylamine" may include, for example, methylamine, ethylamine, n-propylamine, n-butylamine, n-pentylamine and n-hexylamine. The "amidine" may include benzamidine and formamidine. The "thiol" may include straight thiol having 1 to 6 carbon atoms. Specifically, the "thiol" may include, for example, methanethiol, ethanethiol, 1-propanethiol, 1-butanthiol, 1-pentanethiol and 1-hexanthiol. The "thiol derivative" may include alcohol and ether having the same or different straight alkylthiol having 1 to 6 carbon atoms. Specifically, the thiol derivative may include, for example, 2-mercaptoethanol, 4-mercapto-1-butanol, 6-mercapto-1-hexanol, mercaptomethyl ether, 2-mercaptoethyl ether, 3-mercaptopropyl ether, 4-mercaptobutyl ether, 5-mercaptopentyl ether and 6-mercaptohexyl ether. The amount of the acrylonitrile scavenger to be used depends on the kind of oligonucleic acid derivative (24), and may be in the range of 0.8 to 500 mol per mol of 2-cyanoethoxymethyl substituting the 2'-hydroxyl group of each ribose of the oligonucleic acid derivative (24), and preferably in the range of 1 to 10 mol per mol thereof.

(7) Step G:

The step is a step for removing the protecting group of the 5'-hydroxyl group of the oligonucleic acid derivative (25) by allowing an acid to act on the oligonucleic acid derivative (25) produced in Step F.

[Chemical scheme 28]

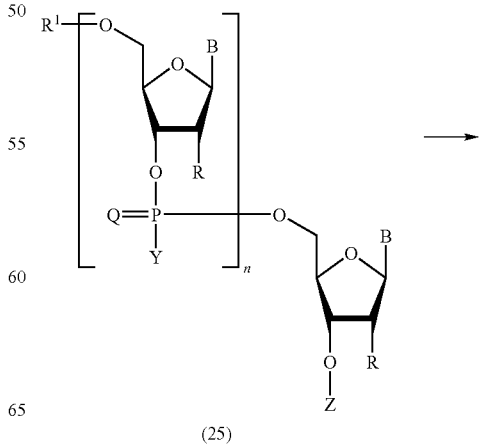

(25)

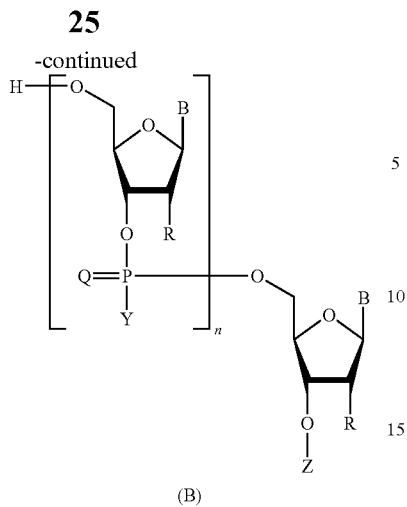

(B)

In formulae (25) and (B), each B, n, each Q, each Y, each R, $R^1$ and Z have the same meanings as described above. When R in the nucleic acid monomer unit constituting the oligo nucleic acid derivative (25) and oligo-RNA (B) is a hydroxyl group, Y represents $O^-$.

The "acid" to be used in the step may include, for example, trichloroacetic acid, dichloroacetic acid and acetic acid. The acid diluted in a suitable solvent can be used in the step. The solvent is not specifically limited unless it is involved in the reaction, and may include, for example, dichloromethane, acetonitrile, water, a buffer whose pH is in the range of 2 to 5 and mixtures thereof. The "buffer solution" may include an acetate buffer. The amount of the reagent to be used may be in the range of 0.8 to 100 mol per mol of the oligonucleic acid derivative attached to the solid support, and is preferably 1 to 10 mol per mol thereof. The reaction temperature in the reaction is preferably in the range of 20° C. to 50° C. The reaction time for deprotection depends on the kind of oligo-nucleic acid derivative (25), the acid, and the reaction temperature, and may be in the range of 1 min to 1 h.

(7) Step H:

The step is a step for isolating and purifying the oligo-RNA (B) produced in Step G.

The "step for isolating and purifying" is a step for isolating and purifying a desired oligo-RNA from the above reaction mixture by a known method, for example, extraction, concentration, neutralization, filtration, centrifugal separation, recrystallization, reverse-phase column chromatography ($C_8$ to $C_{18}$), reverse phase cartridge column chromatography ($C_8$ to $C_{18}$), cation-exchange column chromatography, anion-exchange column chromatography, gel-filtration column chromatography, high performance liquid chromatography, dialysis, ultrafiltration and combinations thereof.

The "eluent" may include acetonitrile, methanol, ethanol, isopropyl alcohol, water and mixtures thereof. In this case, for example, pH of the solution can be controlled to be in the range of pH 1 to 9 by adding sodium phosphate, potassium phosphate, sodium chloride, potassium chloride, ammonium acetate, triethylammonium acetate, sodium acetate, potassium acetate, tris-hydrochloric acid or ethylenediaminetetraacetic acid as an additive in a concentration of 1 mM to 2 M.

The oligoribonucleic acid (B) of desired chain length can be produced by repeating Step A through Step D. In addition, in the method, the nucleic acid derivative (17a) wherein $R^{4a}$ is the substituent (13), the nucleic acid derivative (17a) wherein $R^{4a}$ is H or acyl, or the nucleic acid derivative (17b) wherein $R^2$ is alkyloxy are used. When using the nucleic acid derivative (17a) wherein $R^{4a}$ is H or acyloxy or the nucleic acid derivative (17b) wherein $R^2$ is alkyloxy as a starting material, it is necessary to use one or more units of the phosphoramidite compounds according to the present invention as a nucleic acid monomer compound.

In addition, in the production method, the isolation and purification of an oligo-RNA (B) is also performed by carrying out Step G before Step E, then carrying out Step E, and then Steps F and H.

EXAMPLES

The present invention will now be described in more detail with reference to Examples, to which, however, the present invention is not limited.

Reference Example 1

Methylthiomethyl 2-cyanoethyl ether

3-Hydroxypropionitrile (32 g, 450 mmol) was dissolved in 450 mL of dimethylsulfoxide, and 324 mL of acetic anhydride and 231 mL of acetic acid were added thereto, and the reaction solution was stirred at room temperature for 24 h. Sodium bicarbonate (990 g) was dissolved in 4.5 L of water, and the reaction solution was added dropwise to the aqueous sodium bicarbonate solution over 1 h, and was subjected to extraction with ethyl acetate, and the extract was dried over anhydrous magnesium sulfate, and the solvent was distilled off. The oily product obtained was purified by silica gel column chromatography to give 41 g of methylthiomethyl 2-cyanoethyl ether as a colorless oily product (yield 70%).

$^1$H-NMR (CDCl$_3$): 2.18 (s, 3H), 2.66 (t, 2H, J=6.3 Hz), 3.77 (t, 2H, J=6.3 Hz), 4.69 (s, 2H).

Reference Example 2

2'-O-(2-cyanoethoxymethyl)uridine

Step 1

Production of 3',5'-O-(tetraisopropyldisiloxane-1,3-diyl)-2'-O-(2-cyanoethoxymethyl)uridine 3',5'-O-(Tetraisopropyldisiloxane-1,3-diyl)uridine (150 mg, 0.3 mmol) was dissolved in 7 mL of THF under an argon atmosphere, and 54 mg of methylthiomethyl 2-cyanoethyl ether (0.4 mmol) and 100 mg of Molecular Sieves 4A were added, and the reaction solution was stirred for 10 min. The reaction was performed at 0° C., and 2 mL of a solution of trifluoromethanesulfonic acid (10 mg, 0.06 mmol) in THF was added. Then, 92 mg of N-iodosuccinimide (0.4 mmol) was added and the reaction solution was stirred for 1 h. After completion of the reaction, the reaction solution was filtered through Celite® and washed with dichloromethane, and the organic layer obtained was washed with 1 M aqueous sodium thiosulfate solution. The organic layer was washed with aqueous saturated sodium bicarbonate solution and dried over anhydrous magnesium sulfate, and the solvent was distilled off. The resulting residue was subjected to thin-layer chromatography to give 3',5'-O-(tetraisopropyldisiloxan-1,3-diyl)-2'-O-(2-cyanoethoxymethyl)uridine (150 mg, yield 85%).

$^1$H-NMR (CDCl$_3$): 0.97-1.12 (m, 28H), 2.68-2.73 (m, 2H), 3.78-3.86 (m, 1H), 3.96-4.05 (m, 2H), 4.12-4.30 (m, 4H), 5.0-5.04 (m, 2H), 5.70 (d, 1H, J=8.2 Hz), 5.75 (s, 1H), 7.90 (d, 1H, J=8.2 Hz), 9.62 (brs, 1H).

ESI-Mass: 570[M+H]$^+$

Step 2

Production of 2'-O-(2-cyanoethoxymethyl)uridine

The 3',5'-O-(tetraisopropyldisiloxan-1,3-diyl)-2'-O-(2-cyanoethoxymethyl)uridine (200 mg, 0.35 mmol) obtained in Step 1 was dissolved in 2 mL of methanol, and 65 mg of ammonium fluoride (1.76 mmol) was added thereto, and the reaction solution was stirred with heating at 50° C. for 5 h. After air-cooling, acetonitrile was added to the reaction solution. The solution was stirred, filtered and concentrated. The residue obtained was subjected to silica gel column chromatography to give the desired compound (108 mg, yield 94%).

$^1$H-NMR (CD$_3$OD): 2.72-2.76 (t, 2H, J=6.2 Hz), 3.68-3.92 (m, 4H), 4.00-4.03 (m, 1H), 4.26-4.32 (m, 2H), 4.81-4.95 (m, 2H), 5.71 (d, 1H, J=8.1 Hz), 6.00 (d, 1H, J=3.3 Hz), 8.10 (d, 1H, J=8.1 Hz).

ESI-Mass: 350[M+Na]$^+$

Reference Example 3

2'-O-(2-cyanoethoxymethyl)uridine

Step 1

Production of 3',5'-O-(tetraisopropyldisiloxane-1,3-diyl)-2'-O-(2-cyanoethoxymethyl)uridine 3',5'-O-(Tetraisopropyldisiloxane-1,3-diyl)uridine (50.2 g, 103 mmol) was dissolved in 400 mL of THF under an argon atmosphere, 21.0 g of methylthiomethyl 2-cyanoethyl ether (160 mmol) and 40 g of Molecular Sieves 4A were added, and the reaction solution was dried. The reaction was performed at −45° C., 24 g of trifluoromethanesulfonic acid (160 mmol) was added, then 36.1 g of N-iodosuccinimide (161 mmol) dissolved in 100 mL of THF was added, and the reaction solution was stirred for 15 min. The reaction solution was cooled and triethylamine was added. The reaction solution was then neutralized, filtered at room temperature, and diluted in dichloromethane. The organic layer was washed with aqueous sodium thiosulfate solution and aqueous saturated sodium bicarbonate solution and the solvent was distilled off. The reaction mixture obtained was diluted in ethyl acetate and washed with water and aqueous sodium thiosulfate solution and brine and dried over anhydrous sodium sulfate, and the solvent was distilled off to give 3',5'-O-(tetraisopropyldisiloxan-1,3-diyl)-2'-O-(2-cyanoethoxymethyl)uridine (64.2 g, quantitative yield).

Step 2

Production of 2'-O-(2-cyanoethoxymethyl)uridine

The 3',5'-O-(tetraisopropyldisiloxan-1,3-diyl)-2'-O-(2-cyanoethoxymethyl)uridine (64.2 g, 103 mmol) obtained in Step 1 was dissolved in 500 mL of methanol, 15.3 g of ammonium fluoride (413 mmol) was added, and the reaction solution was stirred with heating at 50° C. for 5 h. After air-cooling, the solvent was distilled off. Acetonitrile was added to the residue, and it was stirred and then filtered. The filtrate was washed with hexane, and the hexane was distilled off to give the desired compound (40.5 g, quantitative yield).

Reference Example 4

N$^4$-acetyl-2'-O-(2-cyanoethoxymethyl)cytidine

Step 1

Production of N$^4$-acetyl-3',5'-O-(tetraisopropyldisiloxane-1,3-diyl)-2'-O-(2-cyanoethoxymethyl)cytidine N$^4$-Acetyl-3',5'-O-(1,3-tetraisopropyldisiloxane-diyl)cytidine 1.00 g (1.89 mmol) and methylthiomethyl 2-cyanoethyl ether 500 mg (3.79 mmol) were mixed, and the mixture was dissolved in mixed solvent of 10 mL of toluene and 10 mL of THF. Subsequently, 975 mg of silver trifluoromethanesulfonate was added and was dried by adding Molecular Sieves 4A. Under ice cooling, 370 mg of N-bromosuccinimide (2.08 mmol) was added, and the solution was stirred for 10 min in the reaction vessel shielded from light. Furthermore, 70 mg of N-bromosuccinimide (0.39 mmol) was added and stirred for 25 min. After completion of the reaction, the reaction solution was diluted with dichloromethane and washed with an aqueous saturated sodium bicarbonate solution. The extract was dried over anhydrous sodium sulfate, and the solvent was distilled off. The mixture obtained was subjected to silica gel column chromatography to give N$^4$-acetyl-3',5'-O-(tetraisopropyldisiloxan-1,3-diyl)-2'-O-(2-cyanoethoxymethyl)cytidine (936 mg, yield 81%).

$^1$H-NMR (CDCl$_3$): 0.90-1.11 (m, 28H), 2.28 (s, 3H), 2.62-2.79 (m, 2H), 3.78-3.89 (m, 1H), 3.96-4.04 (m, 2H), 4.19-4.23 (m, 3H), 4.30 (d, 1H, J=13.6 Hz), 5.00 (d, 1H, J=6.8 Hz), 5.09 (d, 1H, J=6.8 Hz), 5.77 (s, 1H), 7.44 (d, 1H, J=7.5 Hz), 8.30 (d, 1H, J=7.5 Hz), 10.13 (s, 1H).

ESI-Mass: 611[M+H]$^+$

Step 2

Production of N$^4$-acetyl-2'-O-(2-cyanoethoxymethyl)cytidine

The N$^4$-acetyl-3',5'-O-(tetraisopropyldisiloxane-1,3-diyl)-2'-O-(2-cyanoethoxymethyl)cytidine (500 mg, 0.819 mmol) obtained in Step 1 was dissolved in a mixed solvent of 2.5 mL of THF and 2.5 mL of methanol, and 150 mg of ammonium fluoride (4.10 mmol) was added, and then the reaction was allowed to proceed at 50° C. for 4 h. After completion of the reaction, the reaction solution was diluted with acetonitrile and filtered, and the solvent was distilled off. The mixture obtained was subjected to silica gel column chromatography to give the desired compound (210 mg, yield 70%).

$^1$H-NMR (D$_2$O): 2.13 (s, 3H), 2.66-2.71 (m, 2H), 3.72-3.78 (m, 3H), 3.90 (dd, 1H, J=13.0, 2.6 Hz), 4.06-4.11 (m, 1H), 4.20 (dd, 1H, J=7.1, 5.2 Hz), 4.29 (dd, 1H, J=5.1, 2.9 Hz), 4.83 (d, 1H, J=7.2 Hz), 4.94 (d, 1H, J=7.2 Hz), 5.95 (d, 1H, J=2.9 Hz), 7.25 (d, 1H, J=7.6 Hz), 8.25 (d, 1H, J=7.6 Hz).

ESI-Mass: 391[M+Na]$^+$

Reference Example 5

N$^4$-acetyl-2'-O-(2-cyanoethoxymethyl)cytidine

N$^4$-Acetyl-3',5'-O-(1,3-tetraisopropyldisiloxane-diyl)cytidine (50 g, 95 mmol) was dissolved in 500 mL of THF under an argon atmosphere, and 18.64 g of methylthiomethyl 2-cyanoethyl ether (142 mmol) and 40 g of Molecular Sieves 4A were added, and the reaction solution was stirred at −45° C. for 30 min. Trifluoromethanesulfonic acid (21.41 g, 142 mmol) was added dropwise, and then, 31.97 g of N-iodosuccinimide (142 mmol) was added, and the reaction solution was stirred for 30 min. Triethylamine was added to the reaction solution, and reaction solution was filtered. The organic layer was washed with 1 M aqueous sodium thiosulfate solution, aqueous saturated sodium bicarbonate solution and brine, and dried over anhydrous sodium sulfate, and the solvent was distilled off.

The reaction mixture obtained was diluted with 300 mL of THF, 18.3 g of triethylamine trihydrofluoride (110 mmol) were added, and the reaction allowed to proceed at 45° C. for 2 h. The resulting precipitate was filtered, washed with cooled THF and dried to give the desired compound (27 g, yield 78%).

Reference Example 6

$N^6$-acetyl-2'-O-(2-cyanoethoxymethyl)adenosine

Step 1

Production of $N^6$-acetyl-3',5'-O-(tetraisopropyldisiloxan-1,3-diyl)-2'-O-(2-cyanoethoxymethyl)adenosine To 8 mL of dichloromethane was suspended 245 mg of N-iodosuccinimide (1.09 mmol) and 280 mg of silver trifluoromethanesulfonate (1.09 mmol), and the solution was dried by adding Molecular Sieves 4A. To the reaction solution was added a solution of $N^6$-acetyl-3',5'-O-(tetraisopropyldisiloxane-1,3-diyl)adenosine (400 mg, 0.73 mmol) and 145 mg of methylthiomethyl 2-cyanoethyl ether (1.11 mmol) in 4 mL of dichloromethane under ice cooling, and the reaction mixture was stirred for 3 h. After completion of the reaction, the reaction mixture was diluted with dichloromethane, and was washed with aqueous sodium thiosulfate solution and aqueous saturated sodium bicarbonate solution. The extract was dried over anhydrous magnesium sulfate, and the solvent was distilled off. The mixture obtained was subjected to silica gel column chromatography to give $N^6$-acetyl-3',5'-O-(tetraisopropyldisiloxan-1,3-diyl)-2'-O-(2-cyanoethoxymethyl)adenosine (201 mg, yield 45%).

$^1$H-NMR (CDCl$_3$): 0.98-1.11 (m, 28H), 2.62 (s, 3H), 2.69 (td, 2H, 6.5, J=1.5 Hz), 3.81-3.89 (m, 1H), 4.02-4.09 (m, 2H), 4.17 (d, 1H, J=9.4 Hz), 4.28 (d, 1H, J=13.4 Hz), 4.50 (d, 1H, J=4.5 Hz), 4.67 (dd, 1H, J=8.8, 4.5 Hz), 5.02 (d, 1H, J=7.0 Hz), 5.08 (d, 1H, J=7.0 Hz), 6.10 (s, 1H), 8.34 (s, 1H), 8.66 (s, 1H), 8.67 (s, 1H).

ESI-Mass: 636[M+H]$^+$

Step 2

Production of $N^6$-acetyl-2'-O-(2-cyanoethoxymethyl)adenosine

The $N^6$-acetyl-3',5'-O-(tetraisopropyldisiloxane-1,3-diyl)-2'-O-(2-cyanoethoxymethyl)adenosine (300 mg, 0.47 mmol) obtained in Step 1 was dissolved in a mixed solvent of 0.1 mL of acetic acid and 2 mL of 0.5 M TBAF/THF solution, and the reaction solution was stirred at room temperature for 2 h. After completion of the reaction, the reaction mixture was subjected to silica gel column chromatography to give the desired compound (160 mg, yield 86%).

$^1$H-NMR (DMSO-d$_6$): 2.25 (s, 3H), 2.53-2.68 (m, 2H), 3.41-3.46 (m, 1H), 3.56-3.64 (m, 2H), 3.69-3.73 (m, 1H), 4.00-4.01 (m, 1H), 4.36-4.37 (m, 1H), 4.72-4.78 (m, 3H), 5.20 (bt, 2H), 5.41 (d, 1H, J=5.2 Hz), 6.17 (d, 1H, J=5.7 Hz), 8.66 (s, 1H), 8.72 (s, 1H), 10.72 (s, 1H).

ESI-Mass: 415[M+Na]$^+$

Reference Example 7

$N^6$-acetyl-2'-O-(2-cyanoethoxymethyl)adenosine

Step 1

Production of $N^6$-acetyl-3',5'-O-(tetraisopropyldisiloxan-1,3-diyl)-2'-O-methylthiomethyladenosine $N^6$-Acetyl-3',5'-O-(tetraisopropyldisiloxan-1,3-diyl)adenosine (15 g, 17.4 mmol) was dissolved in 100 mL of dimethylsulfoxide, 80 mL of acetic anhydride and 80 mL of acetic acid were added, and the reaction solution was stirred at room temperature overnight. A suspension of 150 g of sodium bicarbonate in 1 L of water was prepared, and the reaction mixture was poured into it, and, after extraction with ethyl acetate, the solvent was distilled off. The residue was redissolved in ethyl acetate and washed with water. The organic layer was dried over anhydrous sodium sulfate and the solvent was distilled off. The mixture obtained was subjected to silica gel column chromatography to give $N^6$-acetyl-3',5'-O-(tetraisopropyldisiloxan-1,3-diyl)-2'-O-methylthiomethyl adenosine (7.2 g; yield 52%).

$^1$H-NMR (CDCl$_3$): 0.96-1.11 (m, 28H); 2.20 (s, 3H); 2.61 (s, 3H); 4.03 (dd, 1H, J=13.4, 2.4 Hz); 4.18 (d, 1H, J=9.1 Hz); 4.27 (d, 1H, J=13.4 Hz); 4.63-4.71 (m, 2H); 5.00 (d, 1H, J=11.5 Hz); 5.07 (d, 1H, J=11.5 Hz); 6.09 (s, 1H); 8.31 (s, 1H); 8.65 (s, 1H); 8.69 (s, 1H).

ESI-Mass: 634 [M+Na]$^+$

Step 2

Production of $N^6$-acetyl-3',5'-O-(tetraisopropyldisiloxan-1,3-diyl)-2'-O-(2-cyanoethoxymethyl)adenosine The $N^6$-acetyl-3',5'-O-(tetraisopropyldisiloxan-1,3-diyl)-2'-O-methylthiomethyl adenosine (49.0 g, 80.1 mmol) obtained in Step 1 and 142 g of 3-hydroxypropionitrile (2.00 mol) were dissolved in 500 mL of THF. The solution was dried by adding Molecular Sieves 4A, and was cooled to −45° C. To the reaction solution was added 21.6 g of N-iodosuccinimide (96.1 mmol) and then 24.2 g of trifluoromethanesulfonic acid (161 mmol), and the reaction solution was stirred at −45° C. for 20 min. After completion of the reaction, the reaction solution was neutralized by adding triethylamine while cooling, and diluted with dichloromethane. The reaction solution was washed with aqueous sodium thiosulfate solution and saturated aqueous sodium bicarbonate solution, and the extract was dried over anhydrous sodium sulfate, and the solvent was distilled off. The reaction mixture obtained was diluted with ethyl acetate. The organic layer was washed with water and brine and dried over anhydrous sodium sulfate, and the solvent was distilled off. The residue obtained was subjected to recrystallization from hexane and ethyl acetate or by silica gel chromatography to give 3',5'-O-(tetraisopropyldisiloxan-1,3-diyl)-2'-O-(2-cyanoethoxymethyl) uridine (45.6 g, yield 90%).

Step 3

Production of $N^6$-acetyl-2'-O-(2-cyanoethoxymethyl)adenosine

The $N^6$-acetyl-3',5'-O-(tetraisopropyldisiloxane-1,3-diyl)-2'-O-(2-cyanoethoxymethyl)adenosine (44 g, 69 mmol) obtained in Step 2 was dissolved in 150 mL of THF, the THF solution was poured into 13.4 g of triethylamine trihydrofluoride dissolved in 50 mL THF, and the reaction solution was stirred at 45° C. for 1 h. After completion of the reaction, 50 mL of hexane was added to the reaction mixture and the solution was stirred under ice cooling. The resulting precipitate was collected by filtration and dried on the filter under aspiration to give the desired compound (29 g, quantitative yield).

Reference Example 8

$N^2$-phenoxyacetyl-2'-O-(2-cyanoethoxymethyl)guanosine

Step 1

Production of $N^2$-phenoxyacetyl-3',5'-O-(tetraisopropyldisiloxane-1,3-diyl)-2'-O-(2-cyanoethoxymethyl)guanosine $N^2$-Phenoxyacetyl-3',5'-O-(1,3-tetraisopropyldisiloxane-1,3-diyl) guanosine (2.0 g, 3.0 mmol) was dissolved in 16 mL of THF, and 0.99 g of methylthiomethyl 2-cyanoethyl ether (7.6 mmol) and 1.0 g of Molecular Sieves 4A were added, and the reaction solution was stirred at −45° C. for 10 min under an argon atmosphere. After a solution of 0.68 g of trifluoromethanesulfonic acid (4.5 mmol) in 5 mL of THF was added and the reaction solution was stirred, 1.02 g of N-iodosuccinimide (4.5 mmol) are added, and the reaction solution was stirred for 15 min. Saturated aqueous sodium bicarbonate solution was added to the reaction solution, the reaction solution was filtered, and the organic layer was washed with 1 M aqueous sodium thiosulfate solution. The reaction solution was then washed sequentially with water and saturated brine, the extract was dried over anhydrous magnesium sulfate, and the solvent was distilled off. The residue obtained was subjected to silica gel chromatography to give $N^2$-phenoxyacetyl-3',5'-O-(tetraisopropyldisiloxan-1,3-diyl)-2'-O-(2-cyanoethoxymethyl)guanosine (2.0 g, yield 89%).

$^1$H-NMR (CDCl$_3$): 0.99-1.11 (m, 28H), 2.59-2.77 (m, 2H), 3.82-4.05 (m, 3H), 4.15 (d, 1H, J=9.3 Hz), 4.25-4.35 (m, 2H), 4.52-4.56 (dd, 1H, J=9.3, 4.3 Hz), 5.00, 5.07 (2d, 2H, J=7.2 Hz), 5.95 (s, 1H) 6.99-7.12 (m, 3H), 7.35-7.40 (m, 2H), 8.09 (s, 1H), 9.38 (brs, 1H), 11.85 (brs, 1H).

ESI-Mass: 766[M+Na]$^+$

Step 2

Production of $N^2$-phenoxyacetyl-2'-O-(2-cyanoethoxymethyl)guanosine

A solution consisting of 0.14 mL of acetic acid (0.14 mmol) and 2.83 mL of 1 M TBAF in THF (2.83 mmol) was prepared. The $N^2$-phenoxyacetyl-3'5'-O-(tetraisopropyldisiloxane-1,3-diyl)-2'-O-(2-cyanoethoxymethyl)guanosine 1.0 g (1.35 mmol) obtained in Step 1 was dissolved in 2.83 mL of THF, and the solution prepared above was added, and the reaction was performed at room temperature for 1 h under an argon atmosphere. The reaction solution was concentrated under reduced pressure, and the residue was dissolved in dichloromethane and subjected to silica gel column chromatography to give the desired compound (0.67 g, yield 99%).

$^1$H-NMR (DMSO-d$_6$): 2.59-2.66 (m, 2H), 3.41-3.63 (m, 4H), 3.98 (m, 1H), 4.32 (m, 1H), 4.58-4.62 (t, 1H, J=5.3 Hz), 4.71-4.78 (dd, 2H, J=13.1, J=6.8 Hz), 4.87 (s, 2H), 5.12 (s, 1H) 5.37 (s, 1H), 5.97 (d, 1H, J=6.1 Hz) 6.96-6.99 (m, 3H), 7.28-7.34 (m, 2H), 8.30 (s, 1H), 11.78 (brs, 2H).

ESI-Mass: 500[M−H]$^-$

Reference Example 9

$N^2$-phenoxyacetyl-2'-O-(2-cyanoethoxymethyl)guanosine

Step 1

Production of $N^2$-phenoxyacetyl-3',5'-O-(tetraisopropyldisiloxane-1,3-diyl)-2'-O-(2-cyanoethoxymethyl)guanosine $N^2$-Phenoxyacetyl-3',5'-O-(1,3-tetraisopropyldisiloxane-1,3-diyl) guanosine (36 g, 55 mmol) was dissolved in 380 mL of THF, and 17.2 g of methylthiomethyl 2-cyanoethyl ether (131 mmol) and 36 g of Molecular Sieves 4A were added, and the reaction solution was stirred at −45° C. for 10 min under an argon atmosphere. After a solution of 12.3 g of trifluoromethanesulfonic acid (82 mmol) was added dropwise to the reaction solution, and then 1.02 g of N-iodosuccinimide (4.5 mmol) are added, and the reaction solution was stirred for 20 min. Saturated aqueous sodium bicarbonate solution was added to the reaction solution, the reaction solution was filtered, and the organic layer was washed with 1 M aqueous sodium thiosulfate solution. The reaction solution was washed sequentially with water and saturated brine, the extract was dried over anhydrous magnesium sulfate, and the solvent was distilled off. The residue obtained was subjected to silica gel chromatography to give $N^2$-phenoxyacetyl-3',5'-O-(tetraisopropyldisiloxan-1,3-diyl)-2'-O-(2-cyanoethoxymethyl)guanosine (32 g, yield 79%).

Step 2

Production of $N^2$-phenoxyacetyl-2'-O-(2-cyanoethoxymethyl)guanosine

The $N^2$-phenoxyacetyl-3'5'-O-(tetraisopropyldisiloxane-1,3-diyl)-2'-O-(2-cyanoethoxymethyl)guanosine (47 g, 63 mmol) obtained in Step 1 was dissolved in 280 mL of acetonitrile, 15.3 g of triethylamine trihydrofluoride (95 mmol) was added, and the reaction solution was stirred at 35° C. for 2 h. After completion of the reaction, the reaction solution was extracted with 100 mL of hexane, water (30 mL) was added to the remaining acetonitrile layer, and the mixture was stirred for 1 h at room temperature. The resulting precipitate was filtered, washed with a mixture of cooled water and acetonitrile (1:1) and dried to give the desired compound (22 g, yield 69%).

Example 1

2'-O-(2-Cyanoethoxymethyl)uridine

3',5'-O-(Tetraisopropyldisiloxan-1,3-diyl)uridine (50.6 g, 104 mmol) was dissolved in 104 mL of THF, then 0.76 mL (10.4 mmol) of methanesulfonic acid, 158 g (624 mmol) of iodine and 16.4 g (125 mmol) of methylthiomethyl 2-cyanoethyl ether were added in an argon atmosphere at 0° C. After 45 min, the reaction solution was added to a mixture of aqueous saturated sodium bicarbonate solution and aqueous saturated sodium thiosulfate solution and extracted with ethyl acetate. The organic layer was washed with aqueous saturated brine, dried over magnesium sulfate and concentrated under reduced pressure to give the crude product.

Methanol (300 mL) was added to the crude product, then 11.6 g of ammonium fluoride was added in an argon gas atmosphere with stirring at room temperature. The temperature was raised to 50° C., followed by stirring for 7.5 h. After completion of the reaction, acetonitrile was added to the reaction mixture and insoluble material was filtered off. The filtrate was washed with hexane and concentrated under reduced pressure to give the desired compound (21.5 g; yield 63%).

Example 2

$N^4$-Acetyl-2'-O-(2-cyanoethoxymethyl)cytidine $N^4$-Acetyl-3',5'-O-(tetraisopropyldisiloxan-1,3-diyl)cytidine (70 g, 133 mmol) was dissolved in 133 mL of THF, then 10.3 mL (160 mmol) of methanesulfonic acid, 201 g (798 mmol) of iodine and 19.9 g (200 mmol) of methylthiomethyl 2-cyanoethyl ether were added in an argon atmosphere at 0° C. After 30 min, the reaction solution was added to a mixture of aqueous saturated sodium bicarbonate solution and aqueous sodium thiosulfate solution for extraction with ethyl acetate. The organic layer was washed with aqueous saturated brine, dried over magnesium sulfate and concentrated under reduced pressure to give the crude product.

THF (266 mL) was added to the crude product, then 25.9 mL of triethylamine trihydrofluoride was added in an argon gas atmosphere with stirring at room temperature. The temperature was raised to 45° C., followed by stirring for 1 h. After completion of the reaction, the reaction mixture was left to stand to allow cooling to room temperature and the formation of a precipitate, which was washed with THF to give the desired compound (42.0 g; yield 86%).

Example 3

$N^6$-Acetyl-2'-O-(2-cyanoethoxymethyl)adenosine $N^4$-Acetyl-3',5'-O-(tetraisopropyldisiloxan-1,3-diyl)adenosine (60 g, 109 mmol) was dissolved in 109 mL of THF, then 1.04 g (10.9 mmol) of methanesulfonic acid, 165.6 g (654 mmol) of iodine and 21.3 g (164 mmol) of methylthiomethyl 2-cyanoethyl ether were added in an argon atmosphere at 0° C. After 2 h, the reaction solution was added to a mixture of aqueous saturated sodium bicarbonate solution and aqueous sodium thiosulfate solution for extraction with ethyl acetate. The organic layer was collected, washed with aqueous saturated brine, dried over magnesium sulfate and concentrated under reduced pressure to give the crude product.

THF (218 mL) was added to the crude product, then 21.3 mL of triethylamine trihydrofluoride was added in an argon gas atmosphere with stirring at room temperature. The temperature was raised to 45° C., followed by stirring for 3 h. After completion of the reaction, the reaction mixture was left to stand to allow cooling to room temperature and the formation of a precipitate, which was collected by filtration and washed with THF and then with a mixture of methanol and ethyl acetate (1:9) to give the desired compound (28.4 g; yield 67%).

Example 4

$N^2$-Phenoxyacetyl-2'-O-(2-cyanoethoxymethyl)guanosine $N^2$-Phenoxyacetyl-3',5'-O-(tetraisopropyldisiloxan-1,3-diyl)guanosine (52.8 g, 80 mmol) was dissolved in 180 mL of THF, then 7.69 g (80 mmol) of methanesulfonic acid, 1.20 g (8 mmol) of trifluoromethanesulfonic acid, 203.0 g (80 mmol) of iodine, and 31.5 g (240 mmol) of methylthiomethyl 2-cyanoethyl ether were added in an argon atmosphere at 0° C. with stirring. After 1 h, the reaction solution was added to a mixture of aqueous saturated sodium bicarbonate solution and aqueous sodium thiosulfate solution for extraction with ethyl acetate. The organic layer was collected, washed with aqueous saturated brine, dried over magnesium sulfate and concentrated under reduced pressure to give the crude product.

THF (170 mL) was added to the crude product, then 15.6 mL of triethylamine trihydrofluoride was added in an argon gas atmosphere, with stirring at room temperature. The temperature was raised to 35° C., followed by stirring for 2 h. After completion of the reaction, the reaction mixture was left to stand to allow cooling to room temperature, then 17 mL of water was added. The precipitate was then collected by filtration to give the target compound (16.7 g; yield 42%).

Example 5

5'-O-(4,4'-Dimethoxytrithyl)-2'-O-(2-cyanoethoxymethyl)-5-methyluridine 3'-O-(2-cyanoethyl N,N-diisopropylphosphoramidite)

Step 1

Production of 3',5'-O-(tetraisopropyldisiloxane-1,3-diyl)-5-methyluridine

Pyridine (300 mL) was added to 27 g (105 mmol) of 5-methyluridine, then 35 g (110 mmol) of 1,3-dichlorotetraisopropyldisiloxane was then added dropwise under ice cooling, followed by stirring at room temperature for 4 h. The reaction solution was concentrated under reduced pressure and extracted with ethyl acetate. The organic layer was washed with aqueous saturated brine, dried over magnesium sulfate and concentrated under reduced pressure to give 3',5'-O-(tetraisopropyldisiloxane-1,3-diyl)-5-methyluridine as a crude product (54.6 g).

Step 2

Production of 2'-O-(2-cyanoethoxymethyl)-5-methyluridine

The crude product from Step 1 (45 g, 89.9 mmol) was dissolved in 90 mL of THF in an argon atmosphere, then 0.58 mL (8.99 mmol) of methanesulfonic acid, 137 g (539 mmol) of iodine, and 14.1 g (107.8 mmol) of methylthiomethyl 2-cyanoethyl ether were added at 0° C. After 30 min, the reaction solution was added to a mixture of aqueous saturated sodium bicarbonate solution and aqueous sodium thiosulfate solution and extracted with ethyl acetate. The organic layer was washed with aqueous saturated brine, dried over magnesium sulfate and concentrated under reduced pressure to give the crude product.

Methanol (250 mL) was added to the crude product, then 10.0 g of ammonium fluoride was added in an argon gas atmosphere with stirring at room temperature. The temperature was raised to 50° C., followed by stirring for 11 h. After completion of the reaction, the reaction mixture was concentrated under reduced pressure, then acetonitrile (300 mL) and methanol (90 mL) were added. Insoluble material was then filtered off. The filtrate was washed with hexane and concentrated under reduced pressure. Precipitation with ethanol (150 mL) gave 2'-O-(2-cyanoethoxymethyl)-5-methyluridine (23.3 g; yield 76%).

$^1$H-NMR (D$_2$O): 1.79 (s, 3H), 2.58-2.74 (m, 2H), 3.68-3.84 (m, 4H), 3.99-4.03 (m, 1H), 4.23-4.32 (m, 2H), 4.74-4.83 (m, 2H), 5.93 (d, 1H, J=3 Hz), 7.62 (s, 1H).

Step 3

Production of 5'-O-(4,4'-dimethoxytrityl)-2'-O-(2-cyanoethoxymethyl)-5-methyluridine To the 2'-O-(2-cyanoethoxymethyl)-5-methyluridine (20.7 g, 60.6 mmol) obtained in Step 2 was added anhydrous tetrahydrofuran (150 mL), anhydrous pyridine (150 mL), activated Molecular Sieves 4A (50 g), and 4,4'-dimethoxytrityl chloride (22.6 g, 66.7 mmol), and the mixture was stirred overnight at room temperature. After completion of the reaction, methanol (5 mL) was added to the reaction solution and the mixture was stirred for 15 min. The reaction solution was then filtered under aspiration and washed with ethyl acetate, and the filtrate was concentrated. To the residue was added aqueous saturated sodium bicarbonate solution and the mixture was extracted with ethyl acetate. The organic layer was washed with aqueous saturated brine, dried over magnesium sulfate, filtered and concentrated. The residue was subjected to silica gel chromatography to give 5'-O-(4,4'-dimethoxytrityl)-2'-O-(2-cyanoethoxymethyl)-5-methyluridine (35.6 g; yield 91.2%).

$^1$H-NMR (CDCl$_3$): 2.05 (s, 1H), 2.62-2.68 (m, 3H), 3.41-3.58 (m, 2H), 3.79 (s, 6H), 3.84 (t, 2H, J=6.1 Hz), 4.03-4.13 (m, 2H, 4.38-4.41 (m, 1H), 4.48-4.54 (m, 1H), 4.91, 5.05 (2d, 2H, J=6.9 Hz), 6.04 (d, 1H, J=3.2 Hz), 6.83-6.86 (m, 4H), 7.22-7.42 (m, 10H), 7.63 (d, 1H, J=1.1 Hz), 8.96 (br.s, 1H).

Step 4

Production of 5'-O-(4,4'-dimethoxytrityl)-2'-O-(2-cyanoethoxymethyl)-5-methyluridine 3'-O-(2-cyanoethyl N,N-diisopropylphosphoramidite)

The 5'-O-(4,4'-dimethoxytrityl)-2'-O-(2-cyanoethoxymethyl)-5-methyluridine obtained in Step 3 (38 g, 59 mmol) was dissolved in anhydrous acetonitrile (350 mL), then activated Molecular Sieves 4A (15 g), diisopropylaminotetrazolide (11.1 g, 64.9 mmol) and bis(N,N-diisopropylamino) cyanoethyl phosphite (19.6 g, 64.9 mmol) were added, and the resulting mixture was stirred at 40° C. for 3 h. The reaction solution was filtered and the filtrate was concentrated. The resulting residue was subjected to silica gel chromatography to give the desired compound (44 g; yield 88%).

$^{31}$P NMR (202 MHz, CDCl$_3$): 152.072, 153.108.

According to the invention, the ribonucleic acid derivative (3) useful as an intermediate for producing various ribonucleic acid derivatives can be produced in large quantities at low cost in a simple manner. Since the reaction can proceed at higher concentrations than when conventional methods are used, the amounts of the reaction solvents needed can be reduced.

In accordance with the invention, therefore, the phosphoramidite compound (A) can be produced economically, and it can be used for producing the oligo RNA (B), useful as RNA probes for gene analysis, raw materials for pharmaceutical RNA products (using antisense RNA, ribozymes, control of gene expression or RNAi), artificial enzymes, and aptamers.

The invention claimed is:

1. A method for producing a ribonucleic acid derivative of formula (3), comprising reacting a ribonucleic acid derivative of formula (1) with a monothioacetal compound of formula (2) to produce the ribonucleic acid derivative of formula (3), wherein iodine is used as a reagent for halogenating the sulfur atom of the monothioacetal compound of formula (2) in the presence of an acid:

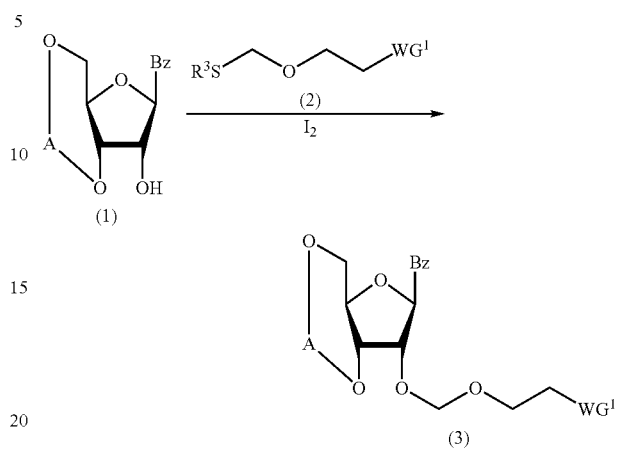

wherein Bz represents a nucleobase optionally having a protecting group; WG$^1$ represents an electron-withdrawing group; R$^3$ represents alkyl or aryl; and A represents a silicon substituent selected from formula (4a) and formula (4b):

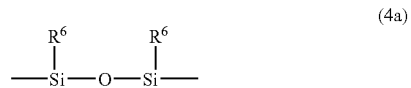

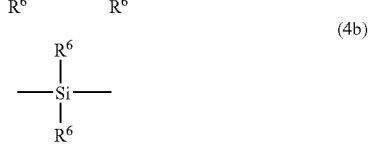

wherein R$^6$ represents alkyl.

2. A method for producing a ribonucleic acid derivative according to claim 1, wherein the acid is methanesulfonic acid or a mixture of trifluoromethanesulfonic acid and methanesulfonic acid.

3. A method for producing a ribonucleic acid derivative according to claim 1, wherein R$^3$ is methyl.

4. A method for producing a ribonucleic acid derivative according to claim 1, wherein WG$^1$ is cyano.

5. A method for producing a phosphoramidite compound of formula (A):

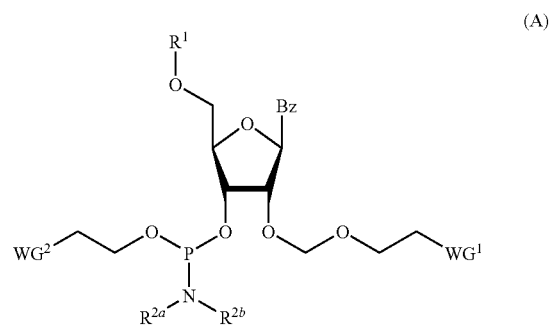

wherein Bz represents a nucleobase optionally having a protecting group; $R^{2a}$ and $R^{2b}$ are the same or different and each represents alkyl, or $R^{2a}$ and $R^{2b}$ form a 5- or 6-membered saturated cyclic amino group when combined together with the adjacent nitrogen atom; the saturated cyclic amino group has one oxygen atom or one sulfur atom as a ring-composing member in addition to the nitrogen atom; $WG^1$ and $WG^2$ are the same or different and each represents an electron-withdrawing group; and $R^1$ represents a substituent of formula (5):

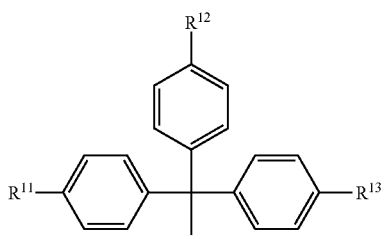

(5)

wherein $R^{11}$, $R^{12}$ and $R^{13}$ are the same or different and each represents hydrogen or alkoxyl; and wherein said method comprises the following step for producing a ribonucleic acid derivative of formula (3), comprising reacting a ribonucleic acid derivative of formula (1) with a monothioacetal compound of formula (2) to produce the ribonucleic acid derivative of formula (3), using iodine as a reagent for halogenating the sulfur atom of the monothioacetal compound (2) in the presence of an acid:

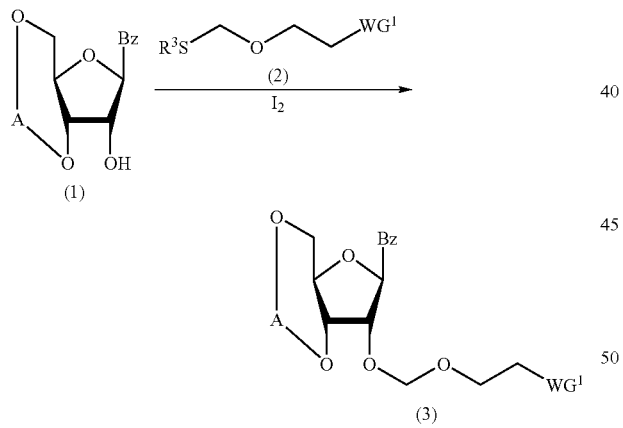

wherein Bz represents a nucleobase optionally having a protecting group; $WG^1$ represents an electron-withdrawing group; $R^3$ represents alkyl or aryl; and A represents a silicon substituent selected from formula (4a) and formula (4b):

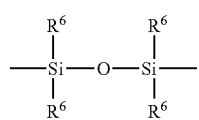

(4a)

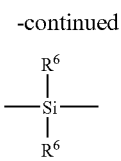

(4b)

wherein $R^6$ represents alkyl.

6. A method for producing a phosphoramidite compound according to claim 5, wherein the acid is methanesulfonic acid or a mixture of trifluoromethanesulfonic acid and methanesulfonic acid.

7. A method for producing a phosphoramidite compound according to claim 5, wherein $R^3$ is methyl.

8. A method for producing a phosphoramidite compound according to claim 5, wherein $WG^1$ is cyano.

9. A method for producing a phosphoramidite compound of formula (A):

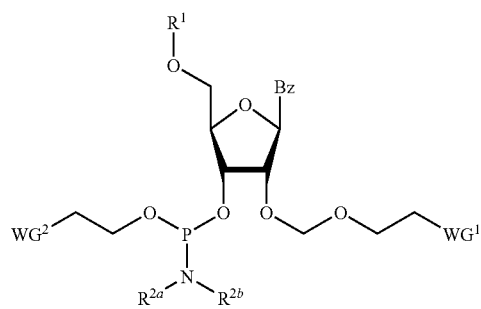

(A)

wherein Bz represents a nucleobase optionally having a protecting group; $R^{2a}$ and $R^{2b}$ are the same or different and each represents alkyl, or $R^{2a}$ and $R^{2b}$ form a 5- or 6-membered saturated cyclic amino group when combined together with the adjacent nitrogen atom; the saturated cyclic amino group has one oxygen atom or one sulfur atom as a ring-composing member in addition to the nitrogen atom; $WG^1$ and $WG^2$ are the same or different and each represents an electron-withdrawing group; and $R^1$ represents a substituent of formula (5):

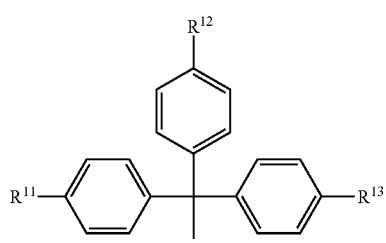

(5)

wherein $R^{11}$, $R^{12}$ and $R^{13}$ are the same or different and each represents hydrogen or alkoxy;

wherein said method comprises the following steps:
(a) a step for producing a ribonucleic acid derivative of formula (3), comprising reacting a ribonucleic acid derivative of formula (1) with a monothioacetal compound of formula (2) to produce the ribonucleic acid derivative of formula (3), using iodine as a reagent for halogenating the sulfur atom of the monothioacetal compound of formula (2) in the presence of an acid:

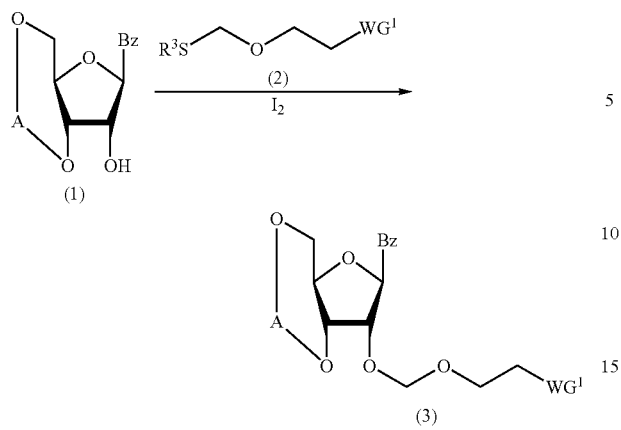

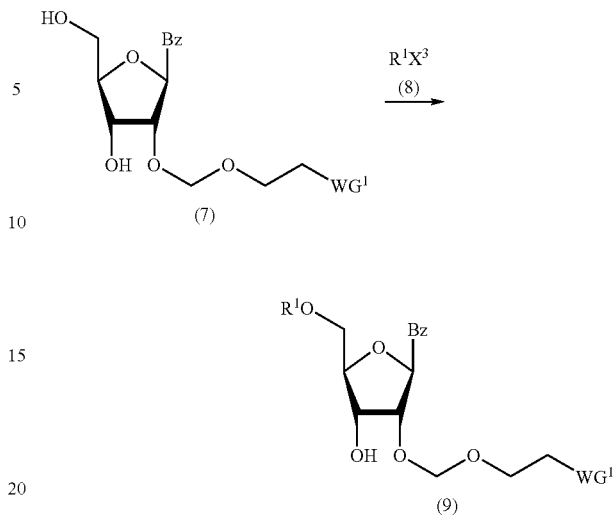

$R^3$ represents alkyl or aryl; and A represents a silicon substituent selected from formula (4a) and formula (4b):

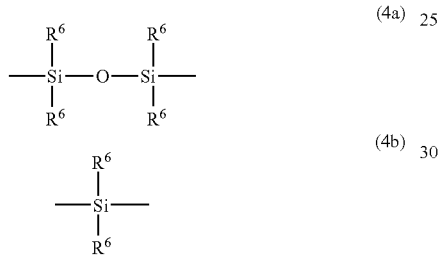

wherein $R^6$ represents alkyl;

(b) a step for producing a ribonucleic acid derivative of formula (7), comprising reacting the ribonucleic acid derivative produced in step (a) with a reagent for removing the silicon substituent:

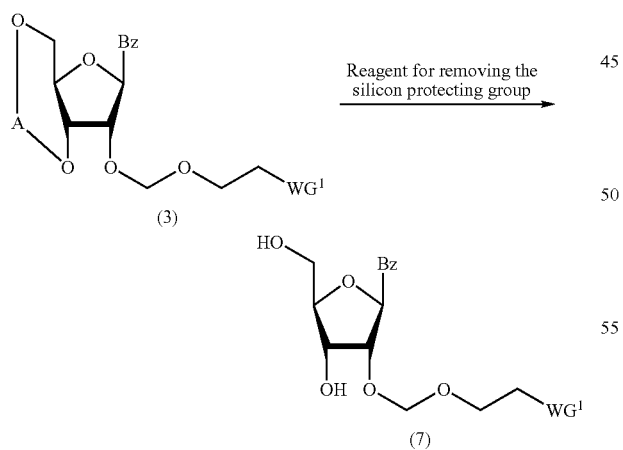

(c) a step for producing a ribonucleic acid derivative of formula (9) comprising reacting the 5'-hydroxyl group of the ribonucleic acid derivative of formula (7) produced in step (b) with $R^1X^3$ of formula (8) to introduce a protecting group, $R^1$, that is removable under acidic conditions:

and $X^3$ represents halogen; and (d) a step for producing a phosphoramidite compound of formula (A), comprising reacting the ribonucleic acid derivative of formula (9) produced in step (c) with a reagent for preparing a phosphoramidite and optionally with an activating agent, to phosphoramidite the ribonucleic acid derivative at the 3'-hydroxyl group:

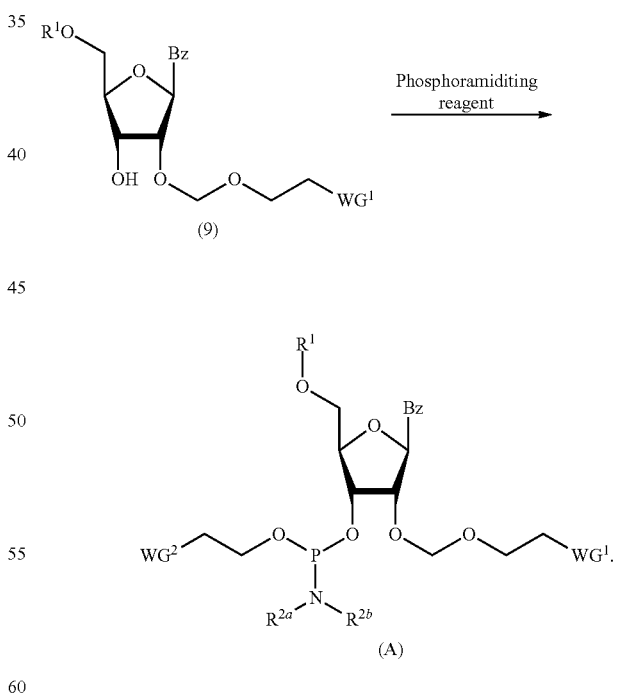

10. A method for producing a phosphoramidite compound according to claim 9, wherein the acid is methanesulfonic acid or a mixture of trifluoromethanesulfonic acid and methanesulfonic acid.

11. A method for producing a phosphoramidite compound according to claim 9, wherein $R^3$ is methyl.

12. A method for producing a phosphoramidite compound according to claim 9, wherein $WG^1$ is cyano.

13. A method for producing a phosphoramidite compound according to claim 9, wherein the reagent for preparing the phosphoramidite is selected from compounds of formula (10a) and formula (10b):

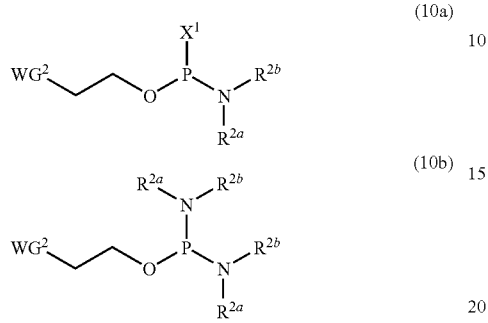

(10a)

(10b)

wherein $R^{2a}$ and $R^{2b}$ are the same or different and each represents alkyl, or $R^{2a}$ and $R^{2b}$ form a 5- or 6-membered saturated cyclic amino group when combined together with the adjacent nitrogen atom; the saturated cyclic amino group has one oxygen atom or one sulfur atom as a ring member in addition to the nitrogen atom; $WG^2$ represents an electron-withdrawing group; and $X^1$ represents halogen.

14. A method for producing a phosphoramidite compound according to claim 9, wherein the activating agent used in step (d) is selected from 1H-tetrazole, 5-ethylthiotetrazole, 5-benzylmercapto-1H-tetrazole, 4,5-dichloroimidazole, 4,5-dicyanoimidazole, benzotriazole triflate, imidazole triflate, pyridinium triflate, N,N-diisopropylethylamine, and 2,4,6-collidine/N-methylimidazole.

15. A method for producing oligo RNA of formula (B) using a phosphoramidite compound produced according to claim 5:

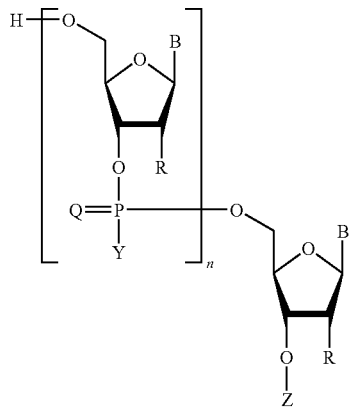

(B)

wherein each B independently represents a nucleobase or a modified product thereof; each Q independently represents O or S; each Y represents alkyl, alkoxy, alkylthio, $O^-$, $S^-$, or $NR^{2a}R^{2b}$, wherein $R^{2a}$ and $R^{2b}$ are the same or different and each represents alkyl, or $R^{2a}$ and $R^{2b}$ form a 5- or 6-membered saturated cyclic amino group when combined together with the adjacent nitrogen atom; the saturated cyclic amino group has one oxygen atom or one sulfur atom as a ring-composing member in addition to the nitrogen atom; each R independently represents H, hydroxyl, halogen, alkoxy, alkylthio, amino, alkylamino, dialkylamino, alkenyloxy, alkenylthio, alkenylamino, dialkenylamino, alkynyloxy, alkynylthio, alkynylamino, dialkynylamino or alkoxyalkyloxy, provided that at least one of the R groups represents hydroxyl; when R in a nucleic acid monomer unit constituting the oligo RNA (B) is hydroxyl, Y represents O; Z represents H, a phosphate group or a thiophosphate group; and n represents an integer in the range of 1 to 200.

* * * * *